(12) United States Patent
Tjarks et al.

(10) Patent No.: US 11,771,712 B2
(45) Date of Patent: *Oct. 3, 2023

(54) CARBORANE COMPOUNDS AND METHODS OF USE THEREOF

(71) Applicants: OHIO STATE INNOVATION FOUNDATION, Columbus, OH (US); INSTITUTE OF MOLECULAR GENETICS AS CR, V.V.I., Prague (CZ)

(72) Inventors: Werner Tjarks, Columbus, OH (US); Petr Bartunek, Prague (CZ); David Sedlak, Prague (CZ)

(73) Assignees: OHIO STATE INNOVATION FOUNDATION, Columbus, OH (US); INSTITUTE OF MOLECULAR GENETICS AS CR, V.V.I., Prague (CZ)

( * ) Notice: Subject to any disclaimer, the term of this patent is extended or adjusted under 35 U.S.C. 154(b) by 151 days.

This patent is subject to a terminal disclaimer.

(21) Appl. No.: 17/241,627

(22) Filed: Apr. 27, 2021

(65) Prior Publication Data

US 2021/0283153 A1 Sep. 16, 2021

Related U.S. Application Data

(63) Continuation of application No. 15/760,971, filed as application No. PCT/US2016/052531 on Sep. 19, 2016, now Pat. No. 11,020,411.

(60) Provisional application No. 62/219,998, filed on Sep. 17, 2015.

(51) Int. Cl.
| | |
|---|---|
| *A61K 31/69* | (2006.01) |
| *A61K 45/06* | (2006.01) |
| *A61K 31/05* | (2006.01) |
| *C07F 5/02* | (2006.01) |
| *A61P 19/02* | (2006.01) |
| *A61P 1/00* | (2006.01) |
| *A61P 35/00* | (2006.01) |

(52) U.S. Cl.
CPC .............. *A61K 31/69* (2013.01); *A61K 31/05* (2013.01); *A61K 45/06* (2013.01); *A61P 1/00* (2018.01); *A61P 19/02* (2018.01); *A61P 35/00* (2018.01); *C07F 5/027* (2013.01); *A61K 2300/00* (2013.01)

(58) Field of Classification Search
CPC ......... C07F 5/027; A61K 31/05; A61K 31/69; A61P 1/00; A61P 19/02; A61P 35/00
See application file for complete search history.

(56) References Cited

U.S. PATENT DOCUMENTS

| | | |
|---|---|---|
| 6,838,574 B1 | 1/2005 | Endo et al. |
| 6,960,648 B2 | 11/2005 | Bonny et al. |
| 7,084,133 B2 | 8/2006 | Kagechika et al. |
| 2002/0035243 A1 | 3/2002 | Imfeld et al. |
| 2002/0120100 A1 | 8/2002 | Bonny et al. |
| 2003/0023118 A1 | 1/2003 | Kanayama et al. |
| 2003/0032594 A1 | 2/2003 | Bonny et al. |
| 2004/0102427 A1 | 5/2004 | Hermsmeyer |
| 2004/0249167 A1 | 12/2004 | Dodge |
| 2008/0161372 A1 | 7/2008 | Rohrer |
| 2014/0303390 A1 | 10/2014 | Brynda et al. |

FOREIGN PATENT DOCUMENTS

| | | |
|---|---|---|
| EP | 1145718 A1 | 10/2001 |
| JP | 2010208996 A | 9/2010 |
| KR | 100884489 B1 | 2/2009 |
| WO | 2000040232 A2 | 7/2000 |
| WO | 2009021978 A2 | 2/2009 |
| WO | 2009035791 A1 | 3/2009 |

OTHER PUBLICATIONS

European Patent Office. Communication pursuant to Article 94(3) EPC in EP Application No. 16847559.8 dated Nov. 25, 2021. 6 pages.
Meanwell, Nicholas A. Synopsis of some recent tactical application of bioisosteres in drug design. Journal of medicinal chemistry. Apr. 28, 2011; 54(8): 2529-91.
Bernardo et al. "The yin and yang of adaptive and maladaptive processes in heart failure." Drug Discovery Today: Therapeutic Strategies, 2013, 9, e163-e172.
Scholz et al. Synthesis of Dicarba-closo-dodecaborane-1-carboxamides. Inorganic Chemistry. 2017, 56, 5510-5513. Full article.
International Search Report and Written Opinion issued in PCT/US2016/52531, dated Dec. 16, 2016.
Extended European Search Report and Opinion. Issued in counterpart application No. EP 16847559.8 dated Mar. 6, 2019. 13 pages.
International Preliminary Report on Patentability issued for International Application No. PCT/US2015/049483, dated Mar. 23, 2017.
International Search Report and Written Opinion issued for International Application No. PCT/US2015/049483, dated Dec. 16, 2016.
Endo, et al., "Boron clusters for medicinal drug design: Selective estrogen receptor modulators bearing carborane", Pure Appl. Chem., 2003, 75(9), 1197-1205.

(Continued)

*Primary Examiner* — Alicia L Otton
(74) *Attorney, Agent, or Firm* — Meunier Carlin & Curfman LLC

(57) ABSTRACT

Disclosed herein are compounds comprising dicarba-closo-dodecaborane. The compounds can be, for example, estrogen receptor beta (ERβ) agonists. In some examples, the compounds can be selective ERβ agonists. Also provided herein are methods of treating, preventing, or ameliorating cancer in a subject, suppressing tumor growth in a subject, treating an inflammatory disease in a subject, treating a neurodegenerative disease in a subject, treating a psychotropic disorder in a subject, or a combination thereof, by administering to a subject a therapeutically effective amount of one or more of the compounds or compositions described herein, or a pharmaceutically acceptable salt thereof.

20 Claims, No Drawings

(56) References Cited

OTHER PUBLICATIONS

Endo, et al., "Potent estrogen agonists based on carborane as a hydrophobic skeletal structure", Chem. & Biology, 2001, 8, 341-355.
Endo, Yasuyuki et al., "Potent Estrogen Receptor Ligands Based on Bisphenols with a Globular Hydrophobic Core", Journal of medicinal Chemistry, 2005, 48(12), 3941-3944.
Fujii, Shinya, et al. "Development of p-carborane-based nonsteroidal progesterone receptor antagonists." Bioorganic & medicinal chemistry 22.19 (2014): 5329-5337.
Harris, , "Estrogen Receptor-Beta: Recent Lessons from Vivo Studies", Molecular Endocrinology, 2007, 21(1), 1-13.
Imamov, et al., "Estrogen Receptor beta in Health and Disease", Biology of Reproduction 2005, 73: 866-871.
Ito et al. "A medium-term rat liver bioassay for rapid in vivo detection of carcinogenic potentials of chemicals," Cancer Sci. 2003, 94(1), 3-8.
Jankowiak, Aleksandra et al., "Practical Synthesis of 1, 12-Difunctionalized o-Carborane for the Investigation of Polar Liquid Crystals", Inorganic Chemistry, 2014, 53(16), 8762-8769.
Nilsson, et al., "Estrogen Receptors: Therapies Targeted to Receptor Subtypes", Nature. Clinical Pharmacology & Therapeutics 89(1), 2011, 44-55.
Ogawa, Takumi, et al. "Synthesis and biological evaluation of p-carborane bisphenols and their derivatives: Structure-activity relationship for estrogenic activity." Bioorganic & medicinal chemistry 17.3 (2009): 1109-1117.
Ohta, et al., "Aliphatic Substitution of o-Carboranyl Phenols Enhances Estrogen Receptor Beta Selectivity", Chem. Pharm. Bull. 2014, 62(4) 386-391.
Ohta, et al., "Enhanced estrogen receptor beta (ERβ) selectivity of fluorinated carborane-containing ER modulators", Bioorganic & Medicinal Chemistry Letters 2013, 23(24):6555-6558.
Ohta, Kiminori et al., "Design and synthesis of carborane-containing estrogen receptor-beta (ERbeta)-selective ligands", Bioorganic & Medicinal Chemistry Letters, 2015, 25, 4174-4178.
Ohta, Kiminori et al., "Structural effects in three-ring mesogenic derivatives of p-carborane and their hydrocarbon analogues", Liquid Crystals, 2004, 31(5), 671-682.
Ok, Kiwon et al., "Facile Docking and Scoring Studies of Carborane Ligands with Estrogen Receptor", Bulletin of the Korean Chemical Society, 2013, 34(4), 1051-1054.
Paterni, et al., "Estrogen Receptors Alpha (ERα) and Beta (ERβ) Subtype-Selective Ligands and Clinical Potential", Steroids. 2014, 13-29.
Pecyna, Jacek, Damian Pociecha, and Piotr Kaszyński. "Zwitterionic pyridinium derivatives of [closo-1-CB9H 0]- and [closo-1-CB11H 2]—as high Δϵ additives to a nematic host." Journal of Materials Chemistry C 2.9 (2014): 1585-1591.
Sedlak, et al., Combinatorial Chemistry & High Throughput Screening 2011, 14: 248-266.
STN Registry database entry for CAS RN 1568923-81-8, which has an entry date of Mar. 14, 2014, Accessed Mar. 21, 2019.
Swedenborg, et al., "Regulation of estrogen receptor beta activity and implications in health and disease", Cell. Mol. Life Sci. 2009, 66: 3873-3894. Abstract.
Thirumamagal, BTS et al., "Receptor-Targeted Liposomal Delivery of Boron-Containing Cholesterol Mimics for Boron Neutron Capture Therapy (BNCT)", Bioconj. Chem. 2006, 17, 1141-1150.

CARBORANE COMPOUNDS AND METHODS OF USE THEREOF

CROSS-REFERENCE TO RELATED APPLICATIONS

This application is a continuation of U.S. application Ser. No. 15/760,971 filed Mar. 16, 2018, which is a national stage application filed under 35 U.S.C. § 371 of PCT/US2016/052531 filed Sep. 19, 2016, which claims priority to and the benefit of U.S. Provisional Application No. 62/219,998, filed Sep. 17, 2015, each of which is hereby incorporated herein by reference in its entirety.

BACKGROUND

Estrogen can influence the growth, differentiation, and functioning of many tissues. For example, estrogens play an important role in the female and male reproductive systems, and also in bone maintenance, the central nervous system, and the cardiovascular system. Because of their beneficial actions in non-reproductive tissues, such as bone, brain, and urogenital tract, estrogens would be ideal drugs if they did not have serious adverse effects, such as increasing the risk of breast cancer, endometrial cancer, thromboembolisms, and strokes.

The physiological functions of estrogenic compounds are modulated largely by the estrogen receptor subtypes alpha (ERα) and beta (ERβ). The activity of the two ER subtypes is controlled by the binding of the endogenous hormone 17β-estradiol or of synthetic nonhormonal compounds to the ligand-binding domain.

In humans, both receptor subtypes are expressed in many cells and tissues, and they can control physiological functions in various organ systems, such as reproductive, skeletal, cardiovascular, and central nervous systems, as well as in specific tissues (such as breast and subcompartments of prostate and ovary). ERα is present mainly in mammary glands, uterus, ovary (thecal cells, bone, male reproductive organs (testes and epididumis), prostate (stroma), liver, and adipose tissue. By contrast, ERβ is found mainly in the prostate (epithelium), bladder, ovary (granulosa cells), colon, adipose tissue, and immune system. Both subtypes are markedly expressed in the cardiovascular and central nervous systems, There are some common physiological roles for both estrogen receptor subtypes, such as in the development and function of the ovaries, and in the protection of the cardiovascular system. The alpha subtypes has a more prominent roles on the mammary gland and uterus, as well as on the preservation of skeletal homeostasis and the regulation of metabolism, The beta subtype seems to have a more pronounced effect on the central nervous and immune systems, and it general counteracts the ERα-promoted cell hyperproliferation in tissues such as breast and uterus.

Compounds that either induce or inhibit cellular estrogen responses have potential value as biochemical tools and candidates for drug development. Most estrogen receptor modulators are non-selective for the ER subtypes, but is has been proposed that compounds with ER subtype selectivity would be useful. However, the development of compounds possessing ER subtype specificity still constitutes a major challenge, as the ligand binding domains of the two subtypes are very similar in structure and amino acid sequence.

SUMMARY

Disclosed herein are compounds comprising dicarba-closo-dodecaborane. Disclosed herein are compounds of Formula I, and pharmaceutically acceptable salts thereof:

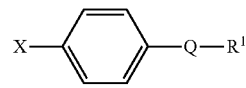

I wherein
Q is a substituted or unsubstituted dicarba-closo-dodecaborane cluster, and

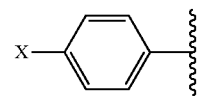

and $R^1$ are attached to Q in a para configuration;

X is OH, $NHR^2$, SH, or $S(O)(O)NHR^2$;

$R^1$ is substituted or unsubstituted $C_4$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ alkylaryl, substituted or unsubstituted $C_4$-$C_{20}$ alkylcycloalkyl, substituted or unsubstituted $C_1$-$C_{20}$ acyl, or $NR^3R^4$;

$R^2$ is H, OH, halogen, or substituted or unsubstituted $C_1$-$C_4$ alkyl;

$R^3$ and $R^4$ are independently selected from substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, or substituted or unsubstituted $C_1$-$C_{20}$ acyl;

with the proviso that when X is OH, $R^1$ is not $(CH_2)_5CH(CH_3)_2$ or $NH_2$.

In some examples of Formula I, the carborane cluster can be substituted with a heteroatom. In some examples of Formula I, the carborane cluster can be substituted with an isotopically labeled atom (i.e., a radiolabeled atom). In some examples of Formula I, the carborane cluster can be isotopically-enriched with one or more boron-10 atoms ($^{10}B$).

In some examples of Formula I, Q can be:

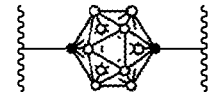

wherein
• is a carbon atom or a boron atom; and
○ is C—H, C-halogen, C-alkyl, C—OH, C—$NH_2$, B—H, B-halogen, B-alkyl, B—OH, or B—$NH_2$.

In some examples of Formula I, X is OH.

In some examples of Formula I, $R^1$ is a substituted or unsubstituted $C_6$-$C_{10}$ alkyl. In some examples of Formula I, $R^1$ is a $C_6$-$C_{10}$ hydroxyalkyl. In some examples of Formula I, $R^1$ is a substituted or unsubstituted $C_3$-$C_{16}$ alkylaryl. In some examples of Formula I, $R^1$ is a $C_3$-$C_{16}$ hydroxyalkylaryl. In some examples of Formula I, $R^1$ is a substituted or unsubstituted $C_8$-$C_{20}$ alkylaryl. In some examples of Formula I, $R^1$ is a substituted or unsubstituted $C_8$-$C_{20}$ alkylcycloalkyl. In some examples of Formula I, $R^1$ is a $C_8$-$C_{20}$ hydroxyalkylarylcycloalkyl. In some examples of Formula I, $R^1$ is a substituted or unsubstituted $C_5$-$C_{10}$ acyl. In some examples of Formula I, $R^1$ is a substituted or unsubstituted branched $C_4$-$C_{10}$ alkyl. In some examples of Formula I, $R^1$ is a branched $C_4$-$C_{10}$ hydroxyalkyl.

In some examples of Formula I, the compounds can be of Formula II, or a pharmaceutically acceptable salt thereof:

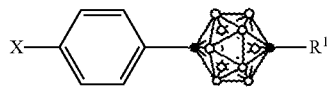

II wherein
- • is a carbon atom;
- ○ is B—H, B-halogen, B-alkyl, B—OH, or B—NH$_2$;

X is OH, NHR$^2$, SH, or S(O)(O)NHR$^2$;

R$^1$ is substituted or unsubstituted C$_4$-C$_{20}$ alkyl, substituted or unsubstituted C$_2$-C$_{20}$ alkenyl, substituted or unsubstituted C$_2$-C$_{20}$ alkynyl, substituted or unsubstituted C$_3$-C$_{20}$ alkylaryl, substituted or unsubstituted C$_4$-C$_{20}$ alkylcycloalkyl, substituted or unsubstituted C$_1$-C$_{20}$ acyl, or NR$^3$R$^4$;

R$^2$ is H, OH, halogen, or substituted or unsubstituted C$_1$-C$_4$ alkyl; and

R$^3$ and R$^4$ are independently selected from substituted or unsubstituted C$_1$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, or substituted or unsubstituted C$_1$-C$_{20}$ acyl;

with the proviso that when X is OH, R$^1$ is not (CH$_2$)$_5$CH(CH$_3$)$_2$ or NH$_2$.

In some examples of Formula II, the carborane cluster can include a heteroatom.

In some examples of Formula II, the carborane cluster can include an isotopically labeled atom (i.e., a radiolabeled atom). In some examples of Formula II, the carborane cluster can include an isotopically labeled Boron atom (e.g., $^{10}$B).

In some examples of Formula II, X is OH.

In some examples of Formula II, R$^1$ is a substituted or unsubstituted C$_6$-C$_{10}$ alkyl. In some examples of Formula II, R$^1$ is a C$_6$-C$_{10}$ hydroxyalkyl. In some examples of Formula II, R$^1$ is a substituted or unsubstituted C$_3$-C$_{16}$ alkylaryl. In some examples of Formula II, R$^1$ is a C$_3$-C$_{16}$ hydroxyalkylaryl. In some examples of Formula II, R$^1$ is a substituted or unsubstituted C$_8$-C$_{20}$ alkylaryl. In some examples of Formula I, R$^1$ is a substituted or unsubstituted C$_8$-C$_{20}$ alkylcycloalkyl. In some examples of Formula II, R$^1$ is a C$_8$-C$_{20}$ hydroxyalkylarylcycloalkyl. In some examples of Formula II, R$^1$ is a substituted or unsubstituted C$_5$-C$_{10}$ acyl. In some examples of Formula II, R$^1$ is a substituted or unsubstituted branched C$_4$-C$_{10}$ alkyl. In some examples of Formula II, R$^1$ is a branched C$_4$-C$_{10}$ hydroxyalkyl.

In some examples of Formula II, the compounds can be of Formula III, or a pharmaceutically acceptable salt thereof:

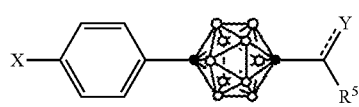

III wherein
- • is a carbon atom;
- ○ is B—H, B-halogen, B-alkyl, B—OH, or B—NH$_2$;
- the dotted line to Y indicates that the bond can be a single bond or a double bond, as valence permits;

X is OH, NHR$^2$, SH, or S(O)(O)NHR$^2$;
Y is O, OR$^{2'}$, NHR$^2$, SH, or S(O)(O)NHR$^2$;

R$^5$ is substituted or unsubstituted C$_2$-C$_{19}$ alkyl, substituted or unsubstituted C$_2$-C$_{19}$ alkenyl, substituted or unsubstituted C$_2$-C$_{19}$ alkynyl, substituted or unsubstituted C$_2$-C$_{19}$ alkylaryl, or substituted or unsubstituted C$_3$-C$_{19}$ alkylcycloalkyl, or NR$^3$R$^4$;

R$^2$ is H, OH, halogen, or substituted or unsubstituted C$_1$-C$_4$ alkyl;

R$^{2'}$ is H or substituted or unsubstituted C$_1$-C$_4$ alkyl; and

R$^3$ and R$^4$ are independently selected from substituted or unsubstituted C$_1$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, or substituted or unsubstituted C$_1$-C$_{20}$ acyl.

In some examples of Formula III, the carborane cluster can include a heteroatom. In some examples of Formula III, the carborane cluster can include an isotopically labeled atom (i.e., a radiolabeled atom). In some examples of Formula III, the carborane cluster can include an isotopically labeled Boron atom (e.g., $^{10}$B).

In some examples of Formula III, X is OH.

In some examples of Formula III, Y is OH. In some examples of Formula III, Y is O.

In some examples of Formula III, R$^5$ is a substituted or unsubstituted C$_3$-C$_9$ alkyl. In some examples of Formula III, R$^5$ is a substituted or unsubstituted C$_6$-C$_9$ alkyl. In some examples of Formula III, R$^5$ is a substituted or unsubstituted C$_2$-C$_{15}$ alkylaryl. In some examples of Formula III, R$^5$ is a substituted or unsubstituted C$_8$-C$_{20}$ alkylarylcycloalkyl. In some examples of Formula III, R$^5$ is a substituted or unsubstituted branched C$_2$-C$_9$ alkyl.

Also disclosed herein are compounds of Formula IV, and pharmaceutically acceptable salts thereof:

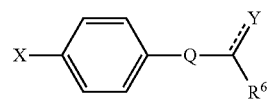

IV wherein

Q is a substituted or unsubstituted dicarba-closo-dodecaborane cluster, and

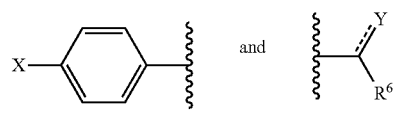

are attached to Q in a para configuration;
the dotted line to Y indicates that the bond can be a single bond or a double bond, as valence permits;

X is OH, NHR$^2$, SH, or S(O)(O)NHR$^2$;
Y is O, OR$^{2'}$, NHR$^2$, SH, or S(O)(O)NHR$^2$;

R$^6$ is substituted or unsubstituted C$_1$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, or substituted or unsubstituted C$_4$-C$_{20}$ alkylcycloalkyl, or NR$^3$R$^4$;

R$^2$ is H, OH, halogen, or substituted or unsubstituted C$_1$-C$_4$ alkyl;

R$^{2'}$ is H or substituted or unsubstituted C$_1$-C$_4$ alkyl; and $R^3$ and $R^4$ are independently selected from substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, or substituted or unsubstituted $C_1$-$C_{20}$ acyl;

with the proviso that when X is OH, $R^6$ is not $CH_2OH$, $CH(CH_3)OH$, $CH_2CH_2OH$, $CH_2CH_2CH_2OH$, $(CH_2)_5CH(CH_3)_2$, or $NH_2$.

In some examples of Formula IV, the carborane cluster can include a heteroatom. In some examples of Formula IV, the carborane cluster can include an isotopically labeled atom (i.e., a radiolabeled atom). In some examples of Formula IV, the carborane cluster can include an isotopically labeled Boron atom (e.g., $^{10}B$).

In some examples of Formula IV, Q can be

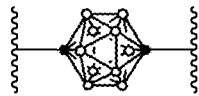

wherein
- • is a carbon atom or a boron atom; and
- ○ is C—H, C-halogen, C-alkyl, C—OH, C—$NH_2$, B—H, B-halogen, B-alkyl, B—OH, or B—$NH_2$.

In some examples of Formula IV, X is OH.

In some examples of Formula IV, Y is OH. In some examples of Formula IV, Y is O.

In some examples of Formula IV, $R^6$ is a substituted or unsubstituted $C_6$-$C_{10}$ alkyl. In some examples of Formula IV, $R^6$ is a substituted or unsubstituted $C_2$-$C_{15}$ alkylaryl. In some examples of Formula IV, $R^6$ is a substituted or unsubstituted $C_8$-$C_{20}$ alkylarylcycloalkyl. In some examples of Formula IV, $R^6$ is a substituted or unsubstituted branched $C_3$-$C_{10}$ alkyl.

In some examples of Formula IV, the compounds can be of Formula V, or a pharmaceutically acceptable salt thereof:

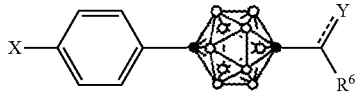

V wherein
- • is a carbon atom;
- ○ is B—H, B-halogen, B-alkyl, B—OH, or B—$NH_2$;

the dotted line to Y indicates that the bond can be a single bond or a double bond, as valence permits;

X is OH, $NHR^2$, SH, or $S(O)(O)NHR^2$;

Y is O, $OR^{2'}$, $NHR^2$, SH, or $S(O)(O)NHR^2$;

$R^6$ is substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, or substituted or unsubstituted $C_4$-$C_{20}$ alkylcycloalkyl, or $NR^3R^4$;

$R^2$ is H, OH, halogen, or substituted or unsubstituted $C_1$-$C_4$ alkyl;

$R^{2'}$ is H or substituted or unsubstituted $C_1$-$C_4$ alkyl; and $R^3$ and $R^4$ are independently selected from substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, or substituted or unsubstituted $C_1$-$C_{20}$ acyl;

with the proviso that when X is OH, $R^6$ is not $CH_2OH$, $CH(CH_3)OH$, $CH_2CH_2OH$, $CH_2CH_2CH_2OH$, $(CH_2)_5CH(CH_3)_2$, or $NH_2$.

In some examples of Formula V, the carborane cluster can include a heteroatom. In some examples of Formula V, the carborane cluster can include an isotopically labeled atom (i.e., a radiolabeled atom). In some examples of Formula V, the carborane cluster can include an isotopically labeled Boron atom (e.g., $^{10}B$).

In some examples of Formula V, X is OH.

In some examples of Formula V, Y is OH. In some examples of Formula V, Y is O.

In some examples of Formula V, $R^6$ is a substituted or unsubstituted $C_6$-$C_{10}$ alkyl. In some examples of Formula V, $R^6$ is a substituted or unsubstituted $C_2$-$C_{15}$ alkylaryl. In some examples of Formula V, $R^6$ is a substituted or unsubstituted $C_8$-$C_{20}$ alkylarylcycloalkyl. In some examples of Formula V, $R^6$ is a substituted or unsubstituted branched $C_3$-$C_{10}$ alkyl.

Also disclosed herein are compounds of Formula VI, and pharmaceutically acceptable salts thereof:

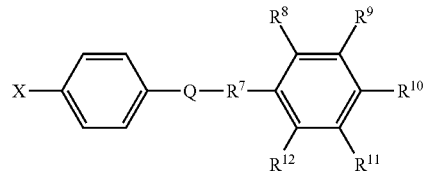

VI wherein
Q is a substituted or unsubstituted dicarba-closo-dodecaborane cluster, and

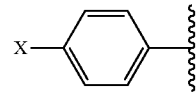

and $R^7$ are attached to Q in a para configuration;

X is OH, $NHR^2$, SH, or $S(O)(O)NHR^2$;

$R^7$ is substituted or unsubstituted $C_1$-$C_{14}$ alkyl, substituted or unsubstituted $C_2$-$C_{14}$ alkenyl, substituted or unsubstituted $C_2$-$C_{14}$ alkynyl, substituted or unsubstituted $C_1$-$C_{14}$ acyl, or $NR^3R^4$;

$R^8$, $R^9$, $R^{10}$, $R^{11}$, and $R^{12}$ are independently H, OH, halogen, substituted or unsubstituted $C_1$-$C_{20}$ alkyl, sub substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, substituted or unsubstituted $C_1$-$C_{20}$ acyl, or $NR^3R^4$, or wherein, as valence permits, $R^8$ and $R^9$, $R^9$ and $R^{10}$, $R^{10}$ and $R^{11}$, or $R^{11}$ and $R^{12}$, together with the atoms to which they are attached, form a 3-10 membered substituted or unsubstituted cyclic moiety optionally including from 1 to 3 heteroatoms;

$R^2$ is H, OH, halogen, or substituted or unsubstituted $C_1$-$C_4$ alkyl; and $R^3$ and $R^4$ are independently selected from substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, or substituted or unsubstituted $C_1$-$C_{20}$ acyl.

In some examples of Formula VI, the carborane cluster can include a heteroatom. In some examples of Formula VI, the carborane cluster can include an isotopically labeled atom (i.e., a radio labeled atom). In some examples of Formula VI, the carborane cluster can include an isotopically labeled Boron atom (e.g., $^{10}B$).

In some examples of Formula VI, Q can be

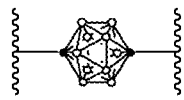

wherein
- • is a carbon atom or a boron atom; and
- ○ is C—H, C-halogen, C-alkyl, C—OH, C—NH$_2$, B—H, B-halogen, B-alkyl, B—OH, or B—NH$_2$.

In some examples of Formula VI, X is OH.

In some examples of Formula VI, $R^7$ is a substituted or unsubstituted $C_1$-$C_7$ alkyl. In some examples of Formula VI, $R^7$ is a $C_1$-$C_7$ hydroxyalkyl.

In some examples of Formula VI, $R^8$-$R^{12}$ are independently H, OH, halogen, or substituted or unsubstituted $C_1$-$C_4$ alkyl, or wherein, as valence permits, $R^8$ and $R^9$, $R^9$ and $R^{10}$, $R^{10}$ and $R^{11}$, or $R^{11}$ and $R^{12}$, together with the atoms to which they are attached, form a 3-10 membered substituted or unsubstituted cyclic moiety optionally including from 1 to 3 heteroatoms. In some examples of Formula VI, $R^8$-$R^{12}$ are each H. In some examples of Formula VI, $R^8$, $R^{10}$, and $R^{12}$ are each H, and $R^9$ and $R^{10}$, together with the atoms to which they are attached, form a substituted or unsubstituted 5-7 membered cyclic moiety.

In some examples of Formula VI, the compounds can be of Formula VII, or a pharmaceutically acceptable salt thereof:

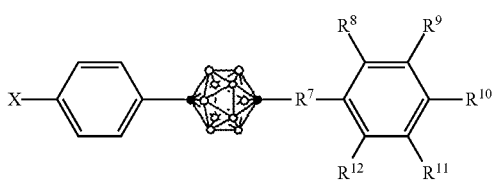

wherein
- • is a carbon atom;
- ○ is B—H, B-halogen, B-alkyl, B—OH, or B—NH$_2$;

X is OH, NHR$^2$, SH, or S(O)(O)NHR$^2$;

$R^7$ is substituted or unsubstituted $C_1$-$C_{14}$ alkyl, substituted or unsubstituted $C_2$-$C_{14}$ alkenyl, substituted or unsubstituted $C_2$-$C_{14}$ alkynyl, substituted or unsubstituted $C_1$-$C_{14}$ acyl, or NR$^3$R$^4$;

$R^8$, $R^9$, $R^{10}$, $R^{11}$, and $R^{12}$ are independently H, OH, halogen, substituted or unsubstituted $C_1$-$C_{20}$ alkyl, sub substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, substituted or unsubstituted $C_1$-$C_{20}$ acyl, or NR$^3$R$^4$, or wherein, as valence permits, $R^8$ and $R^9$, $R^9$ and $R^{10}$, $R^{10}$ and $R^{11}$, or $R^{11}$ and $R^{12}$, together with the atoms to which they are attached, form a 3-10 membered substituted or unsubstituted cyclic moiety optionally including from 1 to 3 heteroatoms;

$R^2$ is H, OH, halogen, or substituted or unsubstituted $C_1$-$C_4$ alkyl; and $R^3$ and $R^4$ are independently selected from substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, or substituted or unsubstituted $C_1$-$C_{20}$ acyl.

In some examples of Formula VII, the carborane cluster can include a heteroatom. In some examples of Formula VII, the carborane cluster can include an isotopically labeled atom (i.e., a radiolabeled atom). In some examples of Formula VII, the carborane cluster can include an isotopically labeled Boron atom (e.g., $^{10}B$).

In some examples of Formula VII, X is OH.

In some examples of Formula VII, $R^7$ is a substituted or unsubstituted $C_1$-$C_7$ alkyl. In some examples of Formula VII, $R^7$ is a $C_1$-$C_7$ hydroxyalkyl.

In some examples of Formula VII, $R^8$-$R^{12}$ are independently H, OH, halogen, or substituted or unsubstituted $C_1$-$C_4$ alkyl, or wherein, as valence permits, $R^8$ and $R^9$, $R^9$ and $R^{10}$, $R^{10}$ and $R^{11}$, or $R^{11}$ and $R^{12}$, together with the atoms to which they are attached, form a 3-10 membered substituted or unsubstituted cyclic moiety optionally including from 1 to 3 heteroatoms. In some examples of Formula VII, $R^8$-$R^{12}$ are each H. In some examples of Formula VII, $R^8$, $R^{10}$, and $R^{12}$ are each H, and $R^9$ and $R^{10}$, together with the atoms to which they are attached, form a substituted or unsubstituted 5-7 membered cyclic moiety.

Also disclosed herein are compounds of Formula VIII, and pharmaceutically acceptable salts thereof:

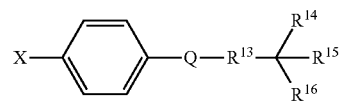

wherein
Q is a substituted or unsubstituted dicarba-closo-dodecaborane cluster, and

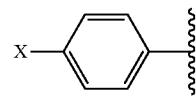

and $R^{13}$ are attached to Q in a para configuration;

X is OH, NHR$^2$, SH, or S(O)(O)NHR$^2$;

$R^{13}$ is substituted or unsubstituted $C_1$-$C_{19}$ alkyl, substituted or unsubstituted $C_2$-$C_{19}$ alkenyl, substituted or unsubstituted $C_2$-$C_{19}$ alkynyl, or substituted or unsubstituted $C_1$-$C_{20}$ acyl; and $R^{14}$, $R^{15}$, and $R^{16}$ are independently hydrogen, halogen, hydroxyl, substituted or unsubstituted $C_1$-$C_{18}$ alkyl, substituted or unsubstituted $C_2$-$C_{18}$ alkenyl, substituted or unsubstituted $C_1$-$C_{18}$ alkynyl, substituted or unsubstituted $C_2$-$C_{18}$ aryl, substituted or unsubstituted $C_3$-$C_{18}$ cycloalkyl, substituted or unsubstituted $C_1$-$C_{20}$ acyl, or NR$^3$R$^4$, or wherein, as valence permits, $R^{14}$ and $R^{15}$, $R^{14}$ and $R^{16}$, or $R^{15}$ and $R^{16}$, together with the atoms to which they are attached, for a 3-10 membered substituted or unsubstituted cyclic moiety optionally including from 1 to 3 heteroatoms, with the proviso that at least two of $R^{14}$, $R^{15}$ and $R^{16}$ are not hydrogen, halogen, or hydroxyl; and with the proviso that when X is OH and $R^{13}$ is a $C_5$ alkyl, $R^{14}$, $R^{15}$, and $R^{16}$ are not H, methyl, and methyl.

In some examples of Formula VIII, the carborane cluster can include a heteroatom. In some examples of Formula VIII, the carborane cluster can include an isotopically labeled atom (i.e., a radio labeled atom). In some examples of Formula VIII, the carborane cluster can include an isotopically labeled Boron atom (e.g., $^{10}B$). In some examples of Formula VIII, Q is

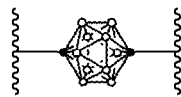

wherein
• is a carbon atom or a boron atom; and
○ is C—H, C-halogen, C-alkyl, C—OH, C—NH$_2$, B—H, B-halogen, B-alkyl, B—OH, or B—NH$_2$.

In some examples of Formula VIII, X is OH.

In some examples of Formula VIII, $R^{13}$ is a substituted or unsubstituted $C_4$-$C_8$ alkyl. In some examples of Formula VIII, $R^{13}$ is a $C_4$-$C_8$ hydroxyalkyl.

In some examples of Formula VIII, $R^{14}$-$R^{16}$ are independently hydrogen, halogen, hydroxyl, substituted or unsubstituted $C_1$-$C_4$ alkyl, with the proviso that at least two of $R^{14}$, $R^{15}$ and $R^{16}$ are not hydrogen, halogen, or hydroxyl; and with the proviso that when X is OH and $R^{13}$ is a $C_5$ alkyl, $R^{14}$, $R^{15}$, and $R^{16}$ are not H, methyl, and methyl.

In some examples of Formula VIII, the compounds can be of Formula IX, or a pharmaceutically acceptable salt thereof:

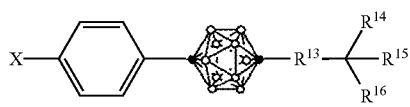

IX wherein
• is a carbon atom;
○ is B—H, B-halogen, B-alkyl, B—OH, or B—NH$_2$;
X is OH, NHR$^2$, SH, or S(O)(O)NHR$^2$;
$R^{13}$ is substituted or unsubstituted $C_1$-$C_{19}$ alkyl, substituted or unsubstituted $C_2$-$C_{19}$ alkenyl, substituted or unsubstituted $C_2$-$C_{19}$ alkynyl, or substituted or unsubstituted $C_1$-$C_{20}$ acyl; and
$R^{14}$, $R^{15}$, and $R^{16}$ are independently hydrogen, halogen, hydroxyl, substituted or unsubstituted $C_1$-$C_{18}$ alkyl, substituted or unsubstituted $C_2$-$C_{18}$ alkenyl, substituted or unsubstituted $C_1$-$C_{18}$ alkynyl, substituted or unsubstituted $C_2$-$C_{18}$ aryl, substituted or unsubstituted $C_3$-$C_{18}$ cycloalkyl, substituted or unsubstituted $C_1$-$C_{20}$ acyl, or NR$^3$R$^4$, or wherein, as valence permits, $R^{14}$ and $R^{15}$, $R^{14}$ and $R^{16}$, or $R^{15}$ and $R^{16}$, together with the atoms to which they are attached, for a 3-10 membered substituted or unsubstituted cyclic moiety optionally including from 1 to 3 heteroatoms, with the proviso that at least two of $R^{14}$, $R^{15}$ and $R^{16}$ are not hydrogen, halogen, or hydroxyl; and with the proviso that when X is OH and $R^{13}$ is a $C_5$ alkyl, $R^{14}$, $R^{15}$, and $R^{16}$ are not H, methyl, and methyl.

In some examples of Formula IX, the carborane cluster can include a heteroatom. In some examples of Formula IX, the carborane cluster can include an isotopically labeled atom (i.e., a radio labeled atom). In some examples of Formula IX, the carborane cluster can include an isotopically labeled Boron atom (e.g., $^{10}B$).

In some examples of Formula IX, X is OH.

In some examples of Formula IX, $R^{13}$ is a substituted or unsubstituted $C_4$-$C_8$ alkyl. In some examples of Formula IX, $R^{13}$ is a $C_4$-$C_8$ hydroxyalkyl.

In some examples of Formula IX, $R^{14}$-$R^{16}$ are independently hydrogen, halogen, hydroxyl, substituted or unsubstituted $C_1$-$C_4$ alkyl, with the proviso that at least two of $R^{14}$, $R^{15}$ and $R^{16}$ are not hydrogen, halogen, or hydroxyl; and with the proviso that when X is OH and $R^{13}$ is a $C_5$ alkyl, $R^{14}$, $R^{15}$, and $R^{16}$ are not H, methyl, and methyl.

In some examples, the compounds can be selected from the group consisting of:

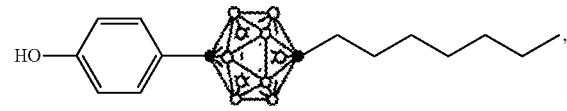

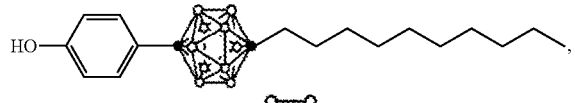

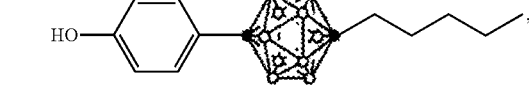

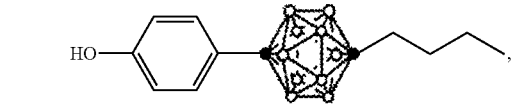

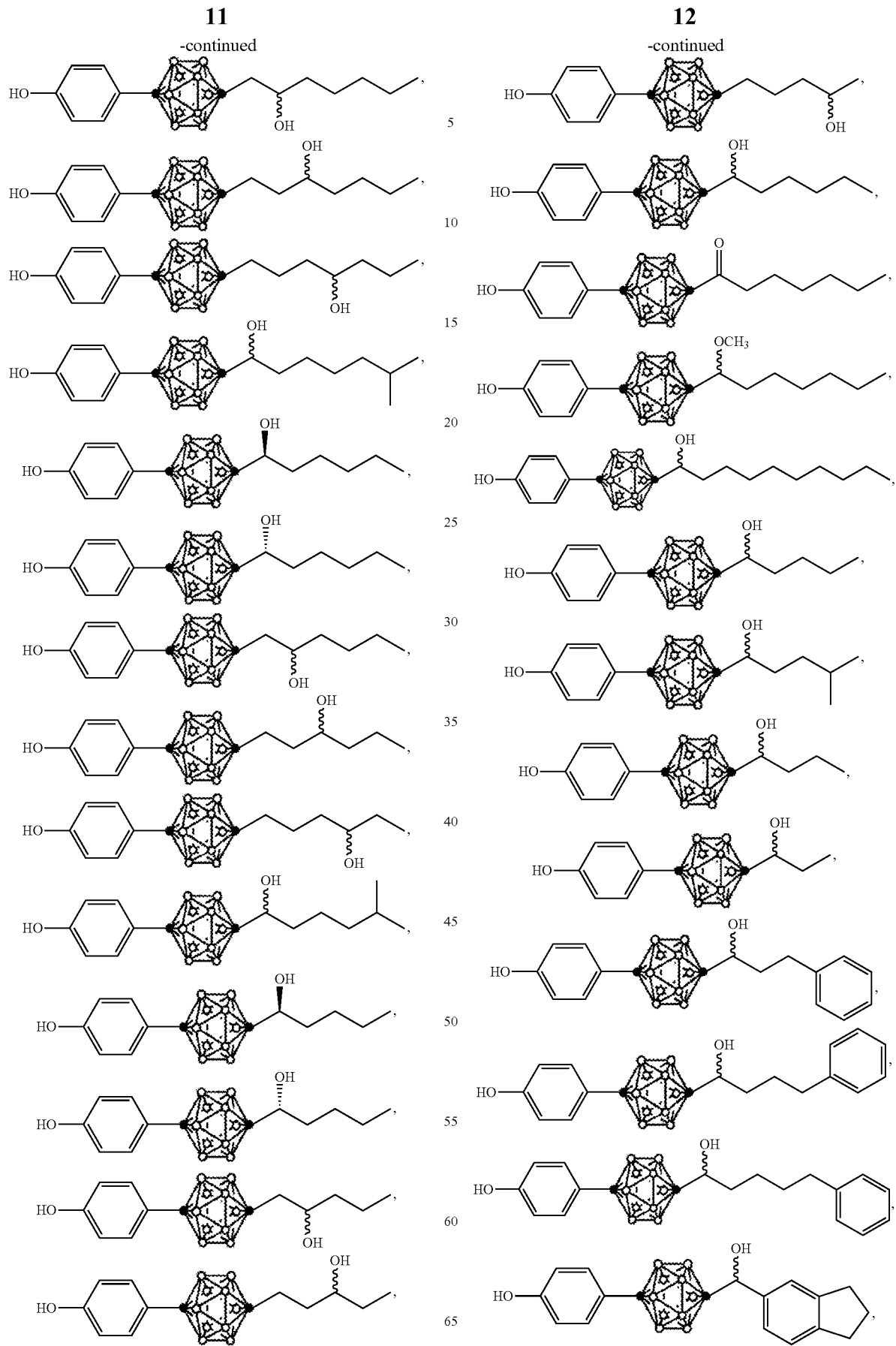

-continued

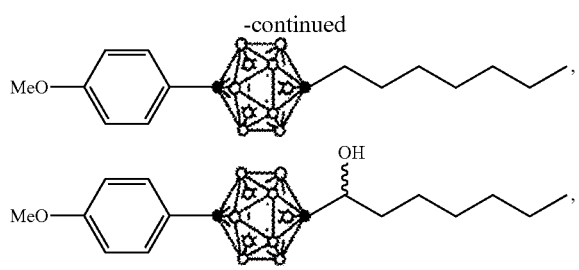

and pharmaceutically acceptable salts thereof. In some examples, the carborane cluster can include a heteroatom. In some examples, the carborane cluster can include an isotopically labeled atom (i.e., a radiolabeled atom). In some examples, the carborane cluster can include an isotopically labeled Boron atom (e.g., $^{10}$B).

In some examples, the compounds disclosed herein can have an $EC_{50}$ of 800 nM or less at estrogen receptor beta (ERβ). In some examples, the compounds disclosed herein can have an an $EC_{50}$ of 6 nM or less at estrogen receptor beta (ERβ). In some examples, the compounds disclosed herein can have an $EC_{50}$ in the subnanomolar range (e.g., an $EC_{50}$ of less than 1 nM, an $EC_{50}$ of 0.5 nM or less, or an $EC_{50}$ of 0.1 nM or less).

In some examples, the compounds disclosed herein can have an ERβ-to-ERα agonist ratio of 8 or more. In some examples, the compounds disclosed herein can have an ERβ-to-ERα agonist ratio of 400 or more.

Some compounds disclosed herein have selectivity for ERβ over ERα and thus exert agonist activity on ERβ without undesired effects on ERα. Therefore the compounds can be used in the treatment of various ERβ-related (ERβ-mediated) diseases, for examples cancers, inflammatory diseases, neurodegenerative diseases, cardiovascular diseases, benign prostate hyperplasia and osteoporosis.

Also provided herein are methods of treating, preventing, or ameliorating cancer in a subject. The methods include administering to a subject a therapeutically effective amount of one or more of the compounds or compositions described herein, or a pharmaceutically acceptable salt thereof. In some examples, the cancer can be selected from the group consisting of breast cancer, colorectal cancer, endometrial cancer, ovarian cancer, and prostate cancer. The methods of treatment or prevention of cancer described herein can further include treatment with one or more additional agents (e.g., an anti-cancer agent or ionizing radiation).

Also described herein are methods of suppressing tumor growth in a subject. The method includes contacting at least a portion of the tumor with a therapeutically effective amount of a compound or composition as described herein, and optionally includes the step of irradiating at least a portion of the tumor with a therapeutically effective amount of ionizing radiation.

Also described herein are methods of treating an inflammatory disease in a subject. The methods can include administering to the subject a therapeutically effective amount of a compound or a composition as described herein. In some examples, the inflammatory disease is selected from the group consisting of arthritis and inflammatory bowel disease. The methods of treatment of inflammatory diseases described herein can further include treatment with one or more additional agents (e.g., an anti-inflammatory agent).

Also disclosed herein are methods of treating a neurodegenerative disease in a subject. The methods can comprise administering to the subject a therapeutically effective amount of a compound or a composition as described herein.

Also disclosed herein are methods of treating a psychotropic disorder in a subject. The methods can comprise administering to the subject a therapeutically effective amount of a compound or a composition as described herein.

Also disclosed herein are methods of imaging a cell or a population of cells expressing ERβ within or about a subject. The methods can comprise administering to the subject an amount of a compound or a composition as described herein; and detecting the compound or the composition.

The details of one or more embodiments of the invention are set forth in the accompanying drawings and the description below. Other features, objects, and advantages of the invention will be apparent from the description and drawings, and from the claims.

DETAILED DESCRIPTION

The compounds, compositions, and methods described herein may be understood more readily by reference to the following detailed description of specific aspects of the disclosed subject matter and the Examples included therein.

Before the present compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient" refers to a subject under the treatment of a clinician, e.g., physician.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "anticancer" refers to the ability to treat or control cellular proliferation and/or tumor growth at any concentration.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Chemical Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ preceding a group or moiety indicates, in each case, the possible number of carbon atoms in the group or moiety that follows.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, heteroatoms present in a compound or moiety, such as nitrogen, can have hydrogen substituents and/or any permissible substituents of organic compounds described herein which satisfy the valency of the heteroatom. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound (e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

As used herein, the term "alkyl" refers to saturated, straight-chained or branched saturated hydrocarbon moieties. Unless otherwise specified, $C_1$-$C_{24}$ (e.g., $C_1$-$C_{22}$, $C_1$-$C_{20}$, $C_1$-$C_{18}$, $C_1$-$C_{16}$, $C_1$-$C_{14}$, $C_1$-$C_{12}$, $C_1$-$C_{10}$, $C_1$-$C_8$, $C_1$-$C_6$, or $C_1$-$C_4$) alkyl groups are intended. Examples of alkyl groups include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl substituents may be unsubstituted or substituted with one or more chemical moieties. The alkyl group can be substituted with one or more groups including, but not limited to, hydroxy, halogen, acyl, alkyl, alkoxy, alkenyl, alkynyl, aryl, heteroaryl, acyl, aldehyde, amino, carboxylic acid, ester, ether, ketone, nitro, silyl, sulfo-oxo, sulfonyl, sulfone, sulfoxide, or thiol, as described below, provided that the substituents are sterically compatible and the rules of chemical bonding and strain energy are satisfied.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halides (halogens; e.g., fluorine, chlorine, bromine, or iodine). The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

As used herein, the term "alkenyl" refers to unsaturated, straight-chained, or branched hydrocarbon moieties containing a double bond. Unless otherwise specified, $C_2$-$C_{24}$ (e.g., $C_2$-$C_{22}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=$CH_2$; 1-propenyl refers to a group with the structure -CH=CH—$CH_3$; and 2-propenyl refers to a group with the structure —$CH_2$—CH=$CH_2$. Asymmetric structures such as $(Z^1Z^2)C$=$C(Z^3Z^4)$ are intended to include both the E and Z isomers. This can be presumed in structural formulae herein wherein an asymmetric alkene is present, or it can be explicitly indicated by the bond symbol C=C. Alkenyl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, or thiol, as described below, provided that the substituents are sterically compatible and the rules of chemical bonding and strain energy are satisfied.

As used herein, the term "alkynyl" represents straight-chained or branched hydrocarbon moieties containing a triple bond. Unless otherwise specified, $C_2$-$C_{24}$ (e.g., $C_2$-$C_{22}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, or thiol, as described below.

As used herein, the term "aryl," as well as derivative terms such as aryloxy, refers to groups that include a monovalent aromatic carbocyclic group of from 3 to 20 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, carboxylic acid, cycloalkyl, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "acyl" as used herein is represented by the formula —C(O)$Z^1$ where $Z^1$ can be a hydrogen, hydroxyl, alkoxy, alkyl, halogenated alkyl, alkenyl, alkynyl, aryl, heteroaryl, cycloalkyl, cycloalkenyl, heterocycloalkyl, or heterocycloalkenyl group described above. As used herein, the term "acyl" can be used interchangeably with "carbo-nyl." Throughout this specification "C(O)" or "CO" is a short hand notation for C=O.

As used herein, the term "alkoxy" refers to a group of the formula $Z^1$—O—, where $Z^1$ is unsubstituted or substituted alkyl as defined above. Unless otherwise specified, alkoxy groups wherein $Z^1$ is a $C_1$-$C_{24}$ (e.g., $C_1$-$C_{22}$, $C_1$-$C_{20}$, $C_1$-$C_{18}$, $C_1$-$C_{16}$, $C_1$-$C_{14}$, $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

The term "aldehyde" as used herein is represented by the formula —C(O)H.

The terms "amine" or "amino" as used herein are represented by the formula —N$Z^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)N$Z^1Z^2$.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1$O$Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1$C(O)$Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" or "halo" as used herein refers to fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH—.

The term "thio" as used herein is represented by the formula —S—.

As used herein, Me refers to a methyl group; OMe refers to a methoxy group; and i-Pr refers to an isopropyl group.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible stereoisomer or mixture of stereoisomer (e.g., each enantiomer, each diastereomer, each meso compound, a racemic mixture, or scalemic mixture).

Reference will now be made in detail to specific aspects of the disclosed materials, compounds, compositions, articles, and methods, examples of which are illustrated in the accompanying Examples and Figures.

Compounds

Disclosed herein are compounds comprising dicarba-closo-dodecaborane. Dicarba-closo-dodecaborane (also referred to herein as "carborane") is an icosahedral cluster containing two carbon atoms and ten boron atoms in which both atoms are hexacoordinated. In carboranes, depending on the position of the carbon atoms in the cluster, 3 kinds of isomers exist, i.e., 1,2-dicarba-closo-dodecaborane (ortho-carborane), 1,7-dicarba-closo-dodecaborane (meta-carborane), and 1,12-dicarba-closo-dodecaborane (para-carborane). These structures are unique among boron compounds, as they can have high thermal stabilities and hydrophobicities, for example, comparable to hydrocarbons.

Carboranes can be used, for example, in $^{10}$Boron-Neutron Capture Therapy (BNCT). BNCT has been developed as a therapy for glioma and melanoma. When $^{10}$B is irradiated with thermal neutron (slow neutron), α ray with 2.4 MeV energy is emitted and the atom decomposed to $^7$Li and $^4$He. The range of α ray is about 10 μm, which corresponds to the diameter of cells Therefore, effects are expected that only cells in which $^{10}$B atoms are uptaken are destroyed and other cells are not damaged. For the development of BNCT, it is important to have cancer cells selectively uptake $^{10}$B atoms in a concentration capable of destroying cells with neutron radiation. For that purpose, other-carborane skeleton has been utilized which has been utilized which has low toxicity and a high $^{10}$B content, and is easy to be synthesized. Moreover, nucleic acid precursors, amino acids, and porphyrins which contain ortho-carboranes have been synthesized and subjected to evaluation.

Disclosed herein are compounds of Formula I, and pharmaceutically acceptable salts thereof:

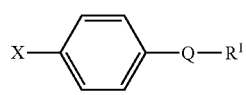

I wherein

Q is a substituted or unsubstituted dicarba-closo-dodecaborane cluster, and

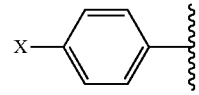

and $R^1$ are attached to Q in a para configuration;

X is OH, $NHR^2$, SH, or $S(O)(O)NHR^2$;

$R^1$ is substituted or unsubstituted $C_4$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ alkylaryl, substituted or unsubstituted $C_4$-$C_{20}$ alkylcycloalkyl, substituted or unsubstituted $C_1$-$C_{20}$ acyl, or $NR^3R^4$;

$R^2$ is H, OH, halogen, or substituted or unsubstituted $C_1$-$C_4$ alkyl;

$R^3$ and $R^4$ are independently selected from substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, or substituted or unsubstituted $C_1$-$C_{20}$ acyl;

with the proviso that when X is OH, $R^1$ is not $(CH_2)_5CH(CH_3)_2$ or $NH_2$.

In some examples of Formula I, the carborane cluster can include a heteroatom. In some examples of Formula I, the carborane cluster can include an isotopically labeled atom (i.e., a radiolabeled atom). In some examples of Formula I, the carborane cluster can include an isotopically labeled Boron atom (e.g., $^{10}$B).

In some examples of Formula I, Q can be:

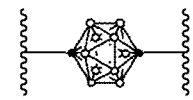

wherein

• is a carbon atom or a boron atom; and

○ is C—H, C-halogen, C-alkyl, C—OH, C—$NH_2$, B—H, B-halogen, B-alkyl, B—OH, or B—$NH_2$.

In some examples of Formula I, X is OH.

In some examples of Formula I, $R^1$ is a substituted or unsubstituted $C_6$-$C_{10}$ alkyl. In some examples of Formula I, $R^1$ is a $C_6$-$C_{10}$ hydroxyalkyl. In some examples of Formula I, $R^1$ is a substituted or unsubstituted $C_3$-$C_{16}$ alkylaryl. In some examples of Formula I, $R^1$ is a $C_3$-$C_{16}$ hydroxyalkylaryl. In some examples of Formula I, $R^1$ is a substituted or unsubstituted $C_5$-$C_{10}$ acyl. In some examples of Formula I, $R^1$ is a substituted or unsubstituted branched $C_4$-$C_{10}$ alkyl. In some examples of Formula I, $R^1$ is a branched $C_4$-$C_{10}$ hydroxyalkyl.

In some examples of Formula I, the compounds can be of Formula II, or a pharmaceutically acceptable salt thereof:

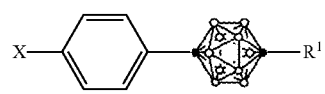

II wherein
- • is a carbon atom;
- ○ is B—H, B-halogen, B-alkyl, B—OH, or B—NH$_2$;

X is OH, NHR$^2$, SH, or S(O)(O)NHR$^2$;

R$^1$ is substituted or unsubstituted C$_4$-C$_{20}$ alkyl, substituted or unsubstituted C$_2$-C$_{20}$ alkenyl, substituted or unsubstituted C$_2$-C$_{20}$ alkynyl, substituted or unsubstituted C$_3$-C$_{20}$ alkylaryl, substituted or unsubstituted C$_4$-C$_{20}$ alkylcycloalkyl, substituted or unsubstituted C$_1$-C$_{20}$ acyl, or NR$^3$R$^4$;

R$^2$ is H, OH, halogen, or substituted or unsubstituted C$_1$-C$_4$ alkyl; and

R$^3$ and R$^4$ are independently selected from substituted or unsubstituted C$_1$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, or substituted or unsubstituted C$_1$-C$_{20}$ acyl;

with the proviso that when X is OH, R$^1$ is not (CH$_2$)$_5$CH(CH$_3$)$_2$ or NH$_2$.

In some examples of Formula II, the carborane cluster can include a heteroatom.

In some examples of Formula II, the carborane cluster can include an isotopically labeled atom (i.e., a radiolabeled atom). In some examples of Formula II, the carborane cluster can include an isotopically labeled Boron atom (e.g., $^{10}$B).

In some examples of Formula II, X is OH.

In some examples of Formula II, R$^1$ is a substituted or unsubstituted C$_6$-C$_{10}$ alkyl. In some examples of Formula II, R$^1$ is a C$_6$-C$_{10}$ hydroxyalkyl. In some examples of Formula II, R$^1$ is a substituted or unsubstituted C$_3$-C$_{16}$ alkylaryl. In some examples of Formula II, R$^1$ is a C$_3$-C$_{16}$ hydroxyalkylaryl. In some examples of Formula II, R$^1$ is a substituted or unsubstituted C$_5$-C$_{10}$ acyl. In some examples of Formula II, R$^1$ is a substituted or unsubstituted branched C$_4$-C$_{10}$ alkyl. In some examples of Formula II, R$^1$ is a branched C$_4$-C$_{10}$ hydroxyalkyl.

In some examples of Formula II, the compounds can be of Formula III, or a pharmaceutically acceptable salt thereof:

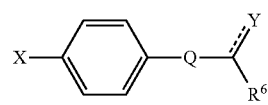

III wherein
- • is a carbon atom;
- ○ is B—H, B-halogen, B-alkyl, B—OH, or B—NH$_2$;

the dotted line to Y indicates that the bond can be a single bond or a double bond, as valence permits;

X is OH, NHR$^2$, SH, or S(O)(O)NHR$^2$;

Y is O, OR$^{2'}$, NHR$^2$, SH, or S(O)(O)NHR$^2$;

R$^5$ is substituted or unsubstituted C$_2$-C$_{19}$ alkyl, substituted or unsubstituted C$_2$-C$_{19}$ alkenyl, substituted or unsubstituted C$_2$-C$_{19}$ alkynyl, substituted or unsubstituted C$_2$-C$_{19}$ alkylaryl, or substituted or unsubstituted C$_3$-C$_{19}$ alkylcycloalkyl, or NR$^3$R$^4$;

R$^2$ is H, OH, halogen, or substituted or unsubstituted C$_1$-C$_4$ alkyl;

R$^{2'}$ is H or substituted or unsubstituted C$_1$-C$_4$ alkyl; and

R$^3$ and R$^4$ are independently selected from substituted or unsubstituted C$_1$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, or substituted or unsubstituted C$_1$-C$_{20}$ acyl.

In some examples of Formula III, the carborane cluster can include a heteroatom. In some examples of Formula III, the carborane cluster can include an isotopically labeled atom (i.e., a radiolabeled atom). In some examples of Formula III, the carborane cluster can include an isotopically labeled Boron atom (e.g., $^{10}$B).

In some examples of Formula III, X is OH.

In some examples of Formula III, Y is OH. In some examples of Formula III, Y is O.

In some examples of Formula III, R$^5$ is a substituted or unsubstituted C$_3$-C$_9$ alkyl. In some examples of Formula III, R$^5$ is a substituted or unsubstituted C$_6$-C$_9$ alkyl. In some examples of Formula III, R$^5$ is a substituted or unsubstituted C$_2$-C$_{15}$ alkylaryl. In some examples of Formula III, R$^5$ is a substituted or unsubstituted branched C$_2$-C$_9$ alkyl.

Also disclosed herein are compounds of Formula IV, and pharmaceutically acceptable salts thereof:

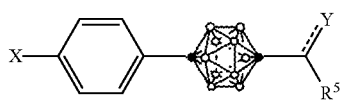

IV wherein

Q is a substituted or unsubstituted dicarba-closo-dodecaborane cluster, and

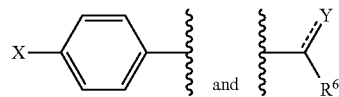

and are attached to Q in a para configuration;

the dotted line to Y indicates that the bond can be a single bond or a double bond, as valence permits;

X is OH, NHR$^2$, SH, or S(O)(O)NHR$^2$;

Y is O, OR$^{2'}$, NHR$^2$, SH, or S(O)(O)NHR$^2$;

R$^6$ is substituted or unsubstituted C$_1$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, or substituted or unsubstituted C$_4$-C$_{20}$ alkylcycloalkyl, or NR$^3$R$^4$;

R$^2$ is H, OH, halogen, or substituted or unsubstituted C$_1$-C$_4$ alkyl;

R$^{2'}$ is H or substituted or unsubstituted C$_1$-C$_4$ alkyl; and

R$^3$ and R$^4$ are independently selected from substituted or unsubstituted C$_1$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, or substituted or unsubstituted C$_1$-C$_{20}$ acyl;

with the proviso that when X is OH, R$^6$ is not CH$_2$OH, CH(CH$_3$)OH, CH$_2$CH$_2$OH, CH$_2$CH$_2$CH$_2$OH, (CH$_2$)$_5$CH(CH$_3$)$_2$, or NH$_2$.

In some examples of Formula IV, the carborane cluster can include a heteroatom. In some examples of Formula IV, the carborane cluster can include an isotopically labeled atom (i.e., a radiolabeled atom). In some examples of Formula IV, the carborane cluster can include an isotopically labeled Boron atom (e.g., $^{10}$B).

In some examples of Formula IV, Q can be

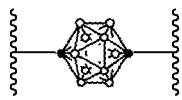

wherein
• is a carbon atom or a boron atom; and
∘ is C—H, C-halogen, C-alkyl, C—OH, C—NH$_2$, B—H, B-halogen, B-alkyl, B—OH, or B—NH$_2$.

In some examples of Formula IV, X is OH.

In some examples of Formula IV, Y is OH. In some examples of Formula IV, Y is O.

In some examples of Formula IV, $R^6$ is a substituted or unsubstituted $C_6$-$C_{10}$ alkyl. In some examples of Formula IV, $R^6$ is a substituted or unsubstituted $C_2$-$C_{15}$ alkylaryl. In some examples of Formula IV, $R^6$ is a substituted or unsubstituted branched $C_3$-$C_{10}$ alkyl.

In some examples of Formula IV, the compounds can be of Formula V, or a pharmaceutically acceptable salt thereof:

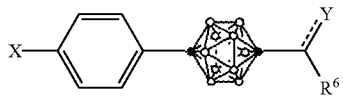

V wherein
• is a carbon atom;
∘ is B—H, B-halogen, B-alkyl, B—OH, or B—NH$_2$;
the dotted line to Y indicates that the bond can be a single bond or a double bond, as valence permits;
X is OH, NHR$^2$, SH, or S(O)(O)NHR$^2$;
Y is O, OR$^{2'}$, NHR$^2$, SH, or S(O)(O)NHR$^2$;
$R^6$ is substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, or substituted or unsubstituted $C_4$-$C_{20}$ alkylcycloalkyl, or NR$^3$R$^4$;
$R^2$ is H, OH, halogen, or substituted or unsubstituted $C_1$-$C_4$ alkyl;
$R^{2'}$ is H or substituted or unsubstituted $C_1$-$C_4$ alkyl; and
$R^3$ and $R^4$ are independently selected from substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, or substituted or unsubstituted $C_1$-$C_{20}$ acyl;
with the proviso that when X is OH, $R^6$ is not CH$_2$OH, CH(CH$_3$)OH, CH$_2$CH$_2$OH, CH$_2$CH$_2$CH$_2$OH, (CH$_2$)$_5$CH (CH$_3$)$_2$, or NH$_2$.

In some examples of Formula V, the carborane cluster can include a heteroatom. In some examples of Formula V, the carborane cluster can include an isotopically labeled atom (i.e., a radiolabeled atom). In some examples of Formula V, the carborane cluster can include an isotopically labeled Boron atom (e.g., $^{10}$B).

In some examples of Formula V, X is OH.

In some examples of Formula V, Y is OH. In some examples of Formula V, Y is O.

In some examples of Formula V, $R^6$ is a substituted or unsubstituted $C_6$-$C_{10}$ alkyl. In some examples of Formula V, $R^6$ is a substituted or unsubstituted $C_2$-$C_{15}$ alkylaryl. In some examples of Formula V, $R^6$ is a substituted or unsubstituted branched $C_3$-$C_{10}$ alkyl.

Also disclosed herein are compounds of Formula VI, and pharmaceutically acceptable salts thereof:

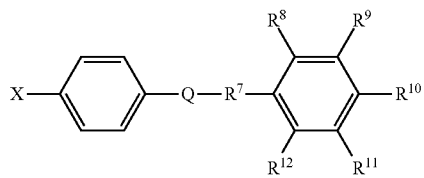

VI wherein
Q is a substituted or unsubstituted dicarba-closo-dodecaborane cluster, and

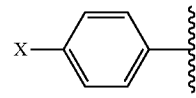

and R$^1$ are attached to Q in a para configuration;
X is OH, NHR$^2$, SH, or S(O)(O)NHR$^2$;
$R^7$ is substituted or unsubstituted $C_1$-$C_{14}$ alkyl, substituted or unsubstituted $C_2$-$C_{14}$ alkenyl, substituted or unsubstituted $C_2$-$C_{14}$ alkynyl, substituted or unsubstituted $C_1$-$C_{14}$ acyl, or NR$^3$R$^4$;
$R^8$, $R^9$, $R^{10}$, $R^{11}$, and $R^{12}$ are independently H, OH, halogen, substituted or unsubstituted $C_1$-$C_{20}$ alkyl, sub substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, substituted or unsubstituted $C_1$-$C_{20}$ acyl, or NR$^3$R$^4$, or wherein, as valence permits, R$^8$ and R$^9$, R$^9$ and R$^{10}$, R$^{10}$ and R$^{11}$, or R$^{11}$ and R$^{12}$, together with the atoms to which they are attached, form a 3-10 membered substituted or unsubstituted cyclic moiety optionally including from 1 to 3 heteroatoms;
$R^2$ is H, OH, halogen, or substituted or unsubstituted $C_1$-$C_4$ alkyl; and
$R^3$ and $R^4$ are independently selected from substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_2$-$C_{20}$ alkylaryl, substituted or unsubstituted $C_4$-$C_{20}$ alkylcycloalkyl, or substituted or unsubstituted $C_1$-$C_{20}$ acyl.

In some examples of Formula VI, the carborane cluster can include a heteroatom. In some examples of Formula VI, the carborane cluster can include an isotopically labeled atom (i.e., a radio labeled atom). In some examples of Formula VI, the carborane cluster can include an isotopically labeled Boron atom (e.g., $^{10}$B).

In some examples of Formula VI, Q can be

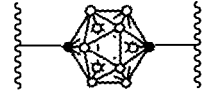

wherein
- • is a carbon atom or a boron atom; and
- ○ is C—H, C-halogen, C-alkyl, C—OH, C—NH$_2$, B—H, B-halogen, B-alkyl, B—OH, or B—NH$_2$.

In some examples of Formula VI, X is OH.

In some examples of Formula VI, R$^7$ is a substituted or unsubstituted C$_1$-C$_7$ alkyl. In some examples of Formula VI, R$^7$ is a C$_1$-C$_7$ hydroxyalkyl.

In some examples of Formula VI, R$^8$-R$^{12}$ are independently H, OH, halogen, or substituted or unsubstituted C$_1$-C$_4$ alkyl, or wherein, as valence permits, R$^8$ and R$^9$, R$^9$ and R$^{10}$, R$^{10}$ and R$^{11}$, or R$^{11}$ and R$^{12}$, together with the atoms to which they are attached, form a 3-10 membered substituted or unsubstituted cyclic moiety optionally including from 1 to 3 heteroatoms. In some examples of Formula VI, R$^8$-R$^{12}$ are each H. In some examples of Formula VI, R$^8$, R$^{10}$, and R$^{12}$ are each H, and R$^9$ and R$^{10}$, together with the atoms to which they are attached, form a substituted or unsubstituted 5-7 membered cyclic moiety.

In some examples of Formula VI, the compounds can be of Formula VII, or a pharmaceutically acceptable salt thereof:

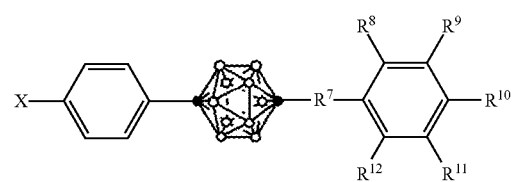

VII wherein
- • is a carbon atom;
- ○ is B—H, B-halogen, B-alkyl, B—OH, or B—NH$_2$;

X is OH, NHR$^2$, SH, or S(O)(O)NHR$^2$;

R$^7$ is substituted or unsubstituted C$_1$-C$_{14}$ alkyl, substituted or unsubstituted C$_2$-C$_{14}$ alkenyl, substituted or unsubstituted C$_2$-C$_{14}$ alkynyl, substituted or unsubstituted C$_1$-C$_{14}$ acyl, or NR$^3$R$^4$;

R$^8$, R$^9$, R$^{10}$, R$^{11}$, and R$^{12}$ are independently H, OH, halogen, substituted or unsubstituted C$_1$-C$_{20}$ alkyl, sub substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, substituted or unsubstituted C$_1$-C$_{20}$ acyl, or NR$^3$R$^4$, or wherein, as valence permits, R$^8$ and R$^9$, R$^9$ and R$^{10}$, R$^{10}$ and R$^{11}$, or R$^{11}$ and R$^{12}$, together with the atoms to which they are attached, form a 3-10 membered substituted or unsubstituted cyclic moiety optionally including from 1 to 3 heteroatoms;

R$^2$ is H, OH, halogen, or substituted or unsubstituted C$_1$-C$_4$ alkyl; and

R$^3$ and R$^4$ are independently selected from substituted or unsubstituted C$_1$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, or substituted or unsubstituted C$_1$-C$_{20}$ acyl.

In some examples of Formula VII, the carborane cluster can include a heteroatom. In some examples of Formula VII, the carborane cluster can include an isotopically labeled atom (i.e., a radiolabeled atom). In some examples of Formula VII, the carborane cluster can include an isotopically labeled Boron atom (e.g., $^{10}$B).

In some examples of Formula VII, X is OH.

In some examples of Formula VII, R$^7$ is a substituted or unsubstituted C$_1$-C$_7$ alkyl. In some examples of Formula VII, R$^7$ is a C$_1$-C$_7$ hydroxyalkyl.

In some examples of Formula VII, R$^8$-R$^{12}$ are independently H, OH, halogen, or substituted or unsubstituted C$_1$-C$_4$ alkyl, or wherein, as valence permits, R$^8$ and R$^9$, R$^9$ and R$^{10}$, R$^{10}$ and R$^{11}$, or R$^{11}$ and R$^{12}$, together with the atoms to which they are attached, form a 3-10 membered substituted or unsubstituted cyclic moiety optionally including from 1 to 3 heteroatoms. In some examples of Formula VII, R$^8$-R$^{12}$ are each H. In some examples of Formula VII, R$^8$, R$^{10}$, and R$^{12}$ are each H, and R$^9$ and R$^{10}$, together with the atoms to which they are attached, form a substituted or unsubstituted 5-7 membered cyclic moiety.

Also disclosed herein are compounds of Formula VIII, and pharmaceutically acceptable salts thereof:

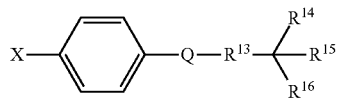

VIII wherein

Q is a substituted or unsubstituted dicarba-closo-dodecaborane cluster, and

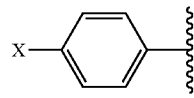

and R$^{13}$ are attached to Q in a para configuration;

X is OH, NHR$^2$, SH, or S(O)(O)NHR$^2$;

R$^{13}$ is substituted or unsubstituted C$_1$-C$_{19}$ alkyl, substituted or unsubstituted C$_2$-C$_{19}$ alkenyl, substituted or unsubstituted C$_2$-C$_{19}$ alkynyl, or substituted or unsubstituted C$_1$-C$_{20}$ acyl; and R$^{14}$, R$^{15}$, and R$^{16}$ are independently hydrogen, halogen, hydroxyl, substituted or unsubstituted C$_1$-C$_{18}$ alkyl, substituted or unsubstituted C$_2$-C$_{18}$ alkenyl, substituted or unsubstituted C$_1$-C$_{18}$ alkynyl, substituted or unsubstituted C$_2$-C$_{18}$ aryl, substituted or unsubstituted C$_3$-C$_{18}$ cycloalkyl, substituted or unsubstituted C$_1$-C$_{20}$ acyl, or NR$^3$R$^4$, or wherein, as valence permits, R$^{14}$ and R$^{15}$, R$^{14}$ and R$^{16}$, or R$^{15}$ and R$^{16}$, together with the atoms to which they are attached, for a 3-10 membered substituted or unsubstituted cyclic moiety optionally including from 1 to 3 heteroatoms, with the proviso that at least two of R$^{14}$, R$^{15}$ and R$^{16}$ are not hydrogen, halogen, or hydroxyl; and with the proviso that when X is OH and R$^{13}$ is a C$_5$ alkyl, R$^{14}$, R$^{15}$, and R$^{16}$ are not H, methyl, and methyl.

In some examples of Formula VIII, the carborane cluster can include a heteroatom. In some examples of Formula VIII, the carborane cluster can include an isotopically labeled atom (i.e., a radio labeled atom). In some examples of Formula VIII, the carborane cluster can include an isotopically labeled Boron atom (e.g., $^{10}$B). In some examples of Formula VIII, Q is

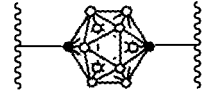

wherein
- • is a carbon atom or a boron atom; and
- ○ is C—H, C-halogen, C-alkyl, C—OH, C—NH$_2$, B—H, B-halogen, B-alkyl, B—OH, or B—NH$_2$.

In some examples of Formula VIII, X is OH.

In some examples of Formula VIII, R$^{13}$ is a substituted or unsubstituted C$_4$-C$_8$ alkyl. In some examples of Formula VIII, R$^{13}$ is a C$_4$-C$_8$ hydroxyalkyl.

In some examples of Formula VIII, R$^{14}$-R$^{16}$ are independently hydrogen, halogen, hydroxyl, substituted or unsubstituted C$_1$-C$_4$ alkyl, with the proviso that at least two of R$^{14}$, R$^{15}$ and R$^{16}$ are not hydrogen, halogen, or hydroxyl; and with the proviso that when X is OH and R$^{13}$ is a C$_5$ alkyl, R$^{14}$, R$^{15}$, and R$^{16}$ are not H, methyl, and methyl.

In some examples of Formula VIII, the compounds can be of Formula IX, or a pharmaceutically acceptable salt thereof:

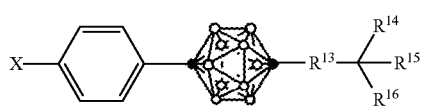

IX wherein
- • is a carbon atom;
- ○ is B—H, B-halogen, B-alkyl, B—OH, or B—NH$_2$;
- X is OH, NHR$^2$, SH, or S(O)(O)NHR$^2$;
- R$^{13}$ is substituted or unsubstituted C$_1$-C$_{19}$ alkyl, substituted or unsubstituted C$_2$-C$_{19}$ alkenyl, substituted or unsubstituted C$_2$-C$_{19}$ alkynyl, or substituted or unsubstituted C$_1$-C$_{20}$ acyl; and
- R$^{14}$, R$^{15}$, and R$^{16}$ are independently hydrogen, halogen, hydroxyl, substituted or unsubstituted C$_1$-C$_{18}$ alkyl, substituted or unsubstituted C$_2$-C$_{18}$ alkenyl, substituted or unsubstituted C$_2$-C$_{18}$ alkynyl, substituted or unsubstituted C$_1$-C$_{18}$ aryl, substituted or unsubstituted C$_3$-C$_{18}$ cycloalkyl, substituted or unsubstituted C$_1$-C$_{20}$ acyl, or NR$^3$R$^4$, or wherein, as valence permits, R$^{14}$ and R$^{15}$, R$^{14}$ and R$^{16}$, or R$^{15}$ and R$^{16}$, together with the atoms to which they are attached, for a 3-10 membered substituted or unsubstituted cyclic moiety optionally including from 1 to 3 heteroatoms, with the proviso that at least two of R$^{14}$, R$^{15}$ and R$^{16}$ are not hydrogen, halogen, or hydroxyl; and with the proviso that when X is OH and R$^{13}$ is a C$_5$ alkyl, R$^{14}$, R$^{15}$, and R$^{16}$ are not H, methyl, and methyl.

In some examples of Formula IX, the carborane cluster can include a heteroatom. In some examples of Formula IX, the carborane cluster can include an isotopically labeled atom (i.e., a radio labeled atom). In some examples of Formula IX, the carborane cluster can include an isotopically labeled Boron atom (e.g., $^{10}$B).

In some examples of Formula IX, X is OH.

In some examples of Formula IX, R$^{13}$ is a substituted or unsubstituted C$_4$-C$_8$ alkyl. In some examples of Formula IX, R$^{13}$ is a C$_4$-C$_8$ hydroxyalkyl.

In some examples of Formula IX, R$^{14}$-R$^{16}$ are independently hydrogen, halogen, hydroxyl, substituted or unsubstituted C$_1$-C$_4$ alkyl, with the proviso that at least two of R$^{14}$, R$^{15}$ and R$^{16}$ are not hydrogen, halogen, or hydroxyl; and with the proviso that when X is OH and R$^{13}$ is a C$_5$ alkyl, R$^{14}$, R$^{15}$, and R$^{16}$ are not H, methyl, and methyl.

In some examples, the compounds can be selected from the group consisting of:

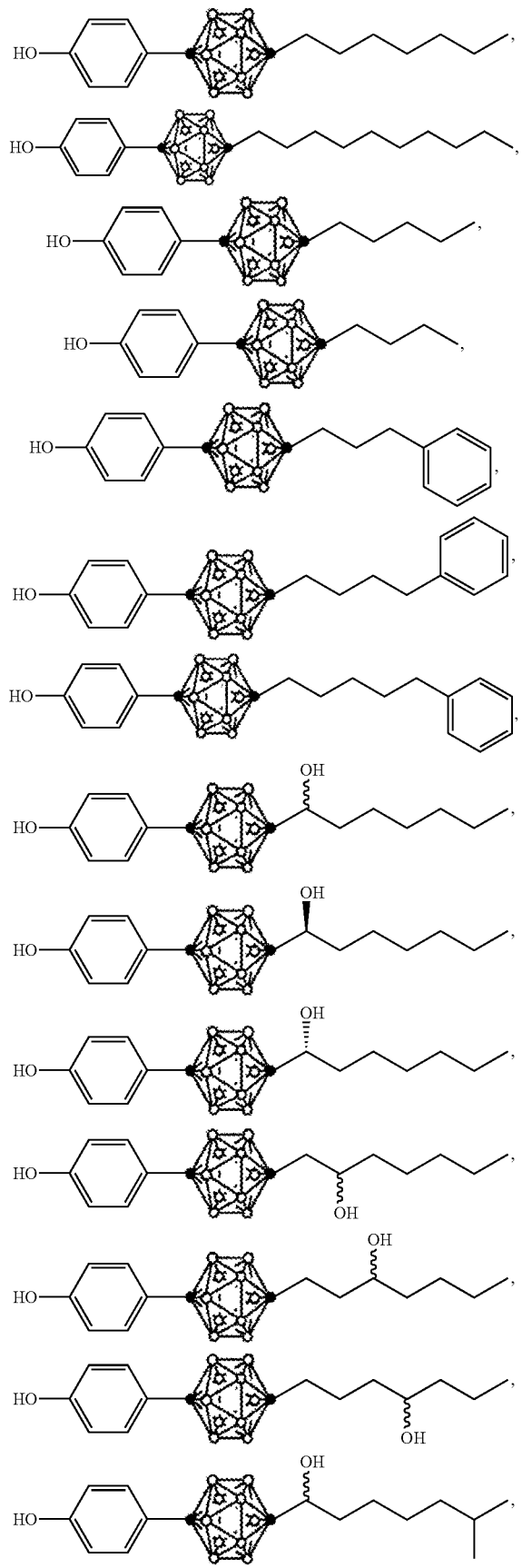

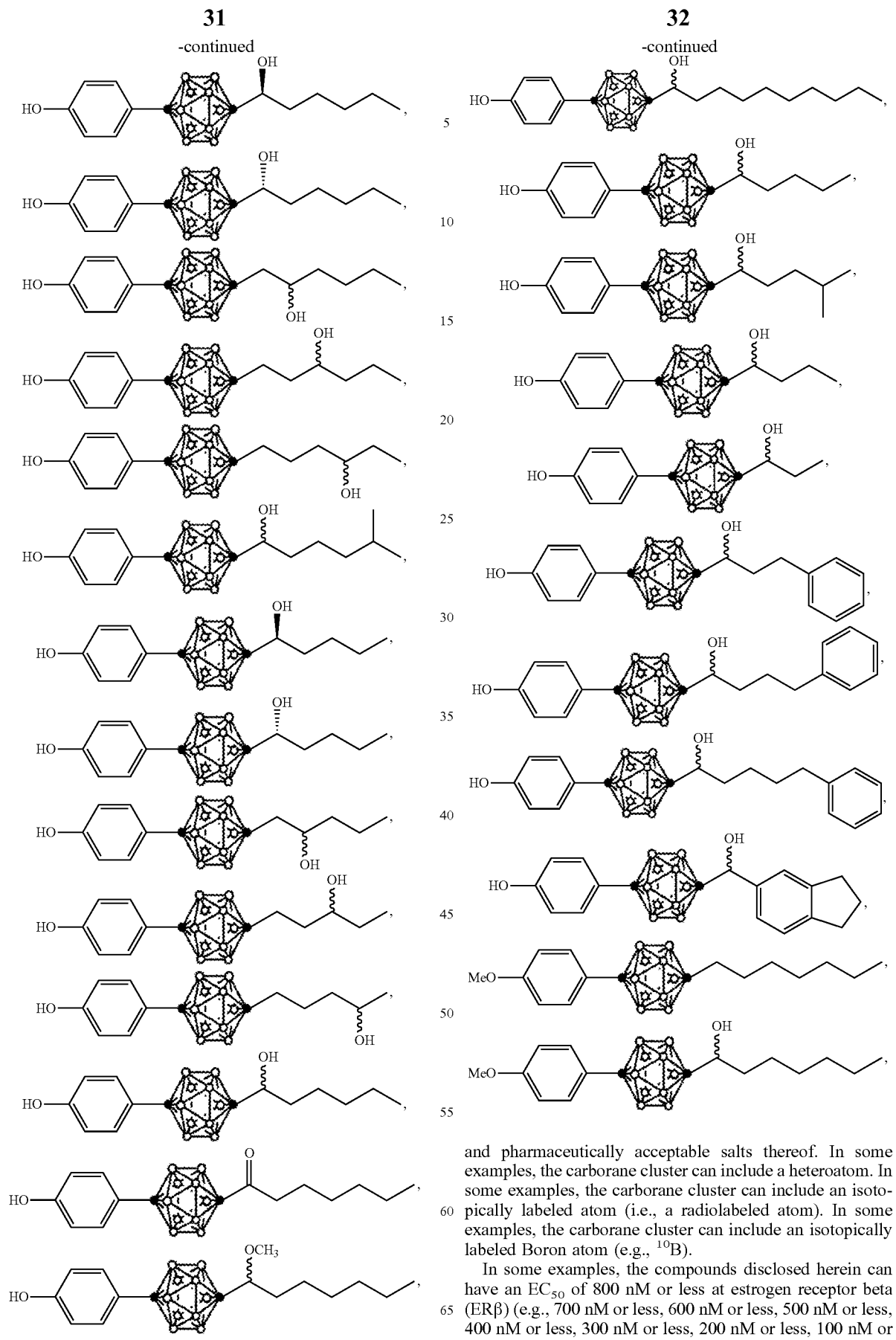

and pharmaceutically acceptable salts thereof. In some examples, the carborane cluster can include a heteroatom. In some examples, the carborane cluster can include an isotopically labeled atom (i.e., a radiolabeled atom). In some examples, the carborane cluster can include an isotopically labeled Boron atom (e.g., $^{10}B$).

In some examples, the compounds disclosed herein can have an $EC_{50}$ of 800 nM or less at estrogen receptor beta (ERβ) (e.g., 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 9 nM or less, 8 nM or less, 7 nM or less, 6 nM or less, 5 nM or less, 4.5 nM or less, 4 nM or less, 3.5 nM or less, 3 nM or less, 2.5 nM or less, 2 nM or less, 1.5 nM or less, 1 nM or less, 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less).

In some examples, the compounds disclosed herein can have an $EC_{50}$ of 1 pM or more at ERβ (e.g., 0.1 nM or more, 0.2 nM or more, 0.3 nM or more, 0.4 nM or more, 0.5 nM or more, 0.6 nM or more, 0.7 nM or more, 0.8 nM or more, 0.9 nM or more, 1 nM or more, 1.5 nM or more, 2 nM or more, 2.5 nM or more, 3 nM or more, 3.5 nM or more, 4 nM or more, 4.5 nM or more, 5 nM or more, 6 nM or more, 7 nM or more, 8 nM or more, 9 nM or more, 10 nM or more, 20 nM or more, 30 nM or more, 40 nM or more, 50 nM or more, 60 nM or more, 70 nM or more, 80 nM or more, 90 nM or more, 100 nM or more, 200 nM or more, 300 nM or more, 400 nM or more, 500 nM or more, 600 nM or more, or 700 nM or more).

The $EC_{50}$ of the compound at ERβ can range from any of the minimum values described above to any of the maximum values described above. For example, the compounds disclosed herein can have an $EC_{50}$ of from 1 pM to 800 nM at ERβ (e.g., from 1 pM to 400 nM, from 400 nM to 800 nM, from 1 pM to 300 nM, from 1 pM to 200 nM, from 1 pM to 100 nM, from 1 pM to 50 nM, from 1 pM to 20 nM, from 1 pM to 10 nM, from 1 pM to 6 nM, from 1 pM to 5 nM, from 1 pM to 2 nM, from 1 pM to 1 nM, from 1 pM to 0.7 nM, from 1 pM to 0.5 nM, from 1 pM to 0.2 pM, or from 1 pM to 0.1 nM).

In some examples, the compounds disclosed herein are selective ERβ agonist. In some examples, a selective ERβ agonist is a compound that has a lower $EC_{50}$ at ERβ than at estrogen receptor α (ERα). The selectivity of the compounds can, in some examples, be expressed as an ERβ-to-ERα agonist ratio, which is the $EC_{50}$ of the compound at ERα divided by the $EC_{50}$ of the compound at ERβ. In some examples, the compounds disclosed herein can have an ERβ-to-ERα agonist ratio of 8 or more (e.g., 10 or more, 20 or more, 30 or more, 40 or more, 50 or more, 60 or more, 70 or more, 80 or more, 90 or more, 100 or more, 150 or more, 200 or more, 250 or more, 300 or more, 350 or more, 400 or more, 450 or more, 500 or more, 600 or more, 700 or more, 800 or more, 900 or more, 1000 or more, 1100 or more, 1200 or more, 1300 or more, 1400 or more, 1500 or more, 2000 or more, 2500 or more).

In some examples, the compounds can have an ERβ-to-ERα agonist ratio of 3000 or less (e.g., 2500 or less, 2000 or less, 1500 or less, 1400 or less, 1300 or less, 1200 or less, 1100 or less, 1000 or less, 900 or less, 800 or less, 700 or less, 600 or less, 500 or less, 450 or less, 400 or less, 350 or less, 300 or less, 250 or less, 200 or less, 150 or less, 100 or less, 90 or less, 80 or less, 70 or less, 60 or less, 50 or less, 40 or less, 30 or less, 20 or less, or 10 or less).

The ERβ-to-ERα agonist ratio of the compounds at ERβ can range from any of the minimum values described above to any of the maximum values described above. For example, the compounds can have an ERβ-to-ERα agonist ratio of from 8 to 3000 (e.g., from 8 to 1500, from 1500 to 3000, from 400 to 3000, from 500 to 3000, from 600 to 3000, from 700 to 3000, from 800 to 3000, from 900 to 3000, from 1000 to 3000, or from 2000 to 3000).

Also disclosed herein are pharmaceutical compositions comprising the compounds described herein, and a pharmaceutically acceptable excipient.

Also disclosed herein are pharmaceutically-acceptable salts and prodrugs of the disclosed compounds. Pharmaceutically-acceptable salts include salts of the disclosed compounds that are prepared with acids or bases, depending on the particular substituents found on the compounds. Under conditions where the compounds disclosed herein are sufficiently basic or acidic to form stable nontoxic acid or base salts, administration of the compounds as salts can be appropriate. Examples of pharmaceutically-acceptable base addition salts include sodium, potassium, calcium, ammonium, or magnesium salt. Examples of physiologically-acceptable acid addition salts include hydrochloric, hydrobromic, nitric, phosphoric, carbonic, sulfuric, and organic acids like acetic, propionic, benzoic, succinic, fumaric, mandelic, oxalic, citric, tartaric, malonic, ascorbic, alpha-ketoglutaric, alpha-glycophosphoric, maleic, tosyl acid, methanesulfonic, and the like. Thus, disclosed herein are the hydrochloride, nitrate, phosphate, carbonate, bicarbonate, sulfate, acetate, propionate, benzoate, succinate, fumarate, mandelate, oxalate, citrate, tartarate, malonate, ascorbate, alpha-ketoglutarate, alpha-glycophosphate, maleate, tosylate, and mesylate salts. Pharmaceutically acceptable salts of a compound can be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Methods of Making

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Katchem (Prague, Czech Republic), Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical excipients disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Methods of Use

Also provided herein are methods of use of the compounds or compositions described herein. Also provided herein are methods for treating a disease or pathology in a subject in need thereof comprising administering to the subject a therapeutically effective amount of any of the compounds or compositions described herein.

Also provided herein are methods of treating, preventing, or ameliorating cancer in a subject. The methods include administering to a subject a therapeutically effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Further examples of cancers treatable by the compounds and compositions described herein include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma. In some examples, the cancer can be selected from the group consisting of breast cancer, colorectal cancer, and prostate cancer.

The methods of treatment or prevention of cancer described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts thereof as described herein can be combined into a pharmaceutical composition with an additional anti-cancer agent, such as 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Oraprex, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PRO- CRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The additional anti-cancer agent can also include biopharmaceuticals such as, for example, antibodies.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease.

Also described herein are methods of suppressing tumor growth in a subject. The method includes contacting at least a portion of the tumor with a therapeutically effective amount of a compound or composition as described herein, and optionally includes the step of irradiating at least a portion of the tumor with a therapeutically effective amount of ionizing radiation. As used herein, the term ionizing radiation refers to radiation comprising particles or photons that have sufficient energy or can produce sufficient energy via nuclear interactions to produce ionization. An example of ionizing radiation is x-radiation. A therapeutically effective amount of ionizing radiation refers to a dose of ionizing radiation that produces an increase in cell damage or death when administered in combination with the compounds described herein. The ionizing radiation can be delivered according to methods as known in the art, including administering radiolabeled antibodies and radioisotopes.

Also described herein are methods of treating an inflammatory disease in a subject. The methods can include administering to the subject a therapeutically effective amount of a compound or a composition as described herein. Inflammatory diseases include, but are not limited to, acne vulgaris, ankylosing spondylitis, asthma, autoimmune diseases, Celiac disease, chronic prostatitis, Crohn's disease, glomerulonephritis, hidradenitis suppurativa, inflammatory bowel diseases, pelvic inflammatory disease, psoriasis, reperfusion injury, rheumatoid arthritis, sarcoidosis, vasculitis, interstitial cystitis, type 1 hypersensitivities, systemic sclerosis, dermatomyositis, polymyositis, and inclusion body myositis. In some examples, the inflammatory disease is selected from the group consisting of arthritis and inflammatory bowel disease.

The methods of treatment of inflammatory diseases described herein can further include treatment with one or more additional agents (e.g., an anti-inflammatory agent). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

Also disclosed herein are methods of treating a neurodegenerative disease in a subject. The methods can comprise administering to the subject a therapeutically effective amount of a compound or a composition as described herein. Neurodegenerative diseases include, but are not limited to, Alzheimer's disease, amyotrophic lateral sclerosis (ALS), Alpers' disease, batten disease, Benson's syndrome, Cerebro-oculo-facio-skeletal (COFS) syndrome, corticobasal degeneration, Creutzfeldt-Jakob disease, dementias, Friedreich's ataxia, Gerstmann-Strussler-Scheinker disease, Huntington's disease, Lewy body syndrome, Leigh's disease, monomelic amyotrophy, motor neuron diseases, multiple system atrophy, opsoclonus myoclonus, progressive multifocal leukoencephalopathy, Parkinson's disease, Prion diseases, primary progressive aphasia, progressive supranuclear palsy, spinocerebellar ataxia, spinal muscular atrophy, kuru, and Shy-Drager syndrome.

Also disclosed herein are methods of treating a psychotropic disorder in a subject. The methods can comprise administering to the subject a therapeutically effective amount of a compound or a composition as described herein. Psychotropic disorders include, but are not limited to, attention deficit disorder (ADD), attention deficit hyperactive disorder (ADHD), anorexia nervosa, anxiety, dipolar disorder, bulimia, depression, insomnia, neuropathic pain, mania, obsessive compulsive disorder (OCD), panic disorder, premenstrual dysphoric disorder (PMDD), mood disorder, serotonin syndrome, schizophrenia, and seasonal affective disorder.

The compounds described herein can also be used to treat other ERβ-related (ERβ-mediated) diseases, including cardiovascular diseases (e.g., heart attack, heart failure, ischemic stroke, arrhythmia), benign prostatic hyperplasia, and osteoporosis.

Also disclosed herein are methods of imaging a cell or a population of cells expressing ERβ within or about a subject. The methods can comprise administering to the subject an amount of a compound or a composition as described herein; and detecting the compound or the composition. The detecting can involve methods known in the art, for example, positron emission tomography *PET), single-photon emission computed tomography (SPECT), magnetic resonance imaging (MRI), X-ray, microscopy, computed tomography (CT). In some examples, the compound or composition can further comprise a detectable label, such as a radiolabel, fluorescent label, enzymatic label, and the like. In some examples, the detectable label can comprise a radiolabel, such as $^{10}B$. Such imaging methods can be used, for example, for assessing the extent of a disease and/or the target of a therapeutic agent.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of the disease or disorder), during early onset (e.g., upon initial signs and symptoms of the disease or disorder), or after an established development of the disease or disorder. Prophylactic administration can occur for several days to years prior to the manifestation of symptoms of a disease or disorder. Therapeutic treatment involves administering to a subject a therapeutically effective amount of the compounds and compositions or pharmaceutically acceptable salts thereof as described herein after the disease or disorder is diagnosed.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that a therapeutically effective amount of the compound is combined with a suitable excipient in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the excipients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; diluents such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Also disclosed are pharmaceutical compositions that comprise a compound disclosed herein in combination with a pharmaceutically acceptable excipient. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

EXAMPLES

The following examples are set forth to illustrate the methods and results according to the disclosed subject matter. These examples are not intended to be inclusive of all aspects of the subject matter disclosed herein, but rather to illustrate representative methods and results. These examples are not intended to exclude equivalents and variations which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

$^1$H- and $^{13}$C-NMR spectra were recorded at The Ohio State University College of Pharmacy using a Bruker AVIII400HD NMR spectrometer or a Bruker DRX400 NMR spectrometer, or at The Ohio State University Campus Chemical Instrumentation Center using a Bruker Ascend 700 MHz NMR at. Chemical shifts (δ) are reported in ppm from internal deuterated chloroform or deuterated acetone. Coupling constants are reported in Hz. $^{13}$C NMR spectra are fully decoupled. NMR spectra were analyzed with Mnova Lite SE (Mestrelab Research, Bajo, Spain). Melting points were obtained on a Thomas Hoover "UNI-MELT" capillary melting apparatus. Optical rotation was measured on a JASCO J-810 spectropolarimeter. Accurate and high resolution mass spectra were obtained from Ohio State University Campus Chemical Instrumentation Center using a Waters Micromass LCT mass spectrometer or a Waters Micromass Q-TOF II mass spectrometer, from The Ohio State University College of Pharmacy using a Waters Micromass Q-TOF micro mass spectrometer or a Thermo LTQ Orbitrap mass spectrometer, or from the University of Illinois Urbana-Champaign Mass Spectrometry Laboratory using a Waters Micromass 70-VSE mass spectrometer. For all carborane-containing compounds, the found mass corresponding to the most intense peak of the theoretical isotopic pattern was reported. Measured patterns agreed with calculated patterns.

Silica gel 60 (0.063-0.200 mm), used for gravity column chromatography. Reagent-grade solvents were used for silica gel column chromatography. Precoated glass-backed TLC plates with silica gel 60 F254 (0.25-mm layer thickness) from Dynamic Adsorbents (Norcross, Ga.) were used for TLC. General compound visualization for TLC was achieved by UV light. Carborane-containing compounds were selectively visualized by spraying the plate with a 0.06% $PdCl_2$/1% HCl solution and heating at 120° C., which caused the slow (15-45 s) formation of a gray spot due to the reduction of $Pd^{2+}$ to $Pd^0$. Chiral analytical HPLC was conducted using a CHIRAL PAK® IB-3 column (250×4.6 mm, 3 m particle size) supplied by Chiral Technologies, PA, USA using on a Hitachi HPLC system (L-2130) with a Windows based data acquisition and Hitachi Diode array detector (L-2455). HPLC-grade solvents were used for HPLC.

Anhydrous solvents for reactions were purchased directly from Acros Organics (Morris Plains, N.J.) or from Sigma Aldrich (Milwaukee, Wis.). Other solvents and chemicals were obtained from standard vendors. Unless specified otherwise, all reactions were carried out under argon atmosphere.

Example 1

To a solution of 1-(4-methoxyphenyl)-1,12-dicarba-closo-dodecaborane (Endo Y et al. *Chemistry & Biology,* 2001, 8, 341-355) (500 mg, 2 mmol) in anhydrous dimethoxyethane (DME, 40 mL) was added n-butyllithium (1 mL, 2.5 mmol, 2.5 M solution in hexanes) at 0° C. The reaction mixture was stirred at room temperature for 1.5 h. A quantity of 0.49 mL (3.0 mmol) 1-iodoheptane was added at 0° C. Following stirring at room temperature for 4 h, the reaction mixture was carefully poured into 60 mL of 1 M HCl and extracted with ethyl acetate. The organic phase was washed with a 10% sodium thiosulfate solution and brine and dried over $MgSO_4$. The solvents were evaporated and the residue purified by silica gel column chromatography (hexanes, $R_f$: 0.38) to yield 550 mg (79%) product as a white solid which had a melting point of 45-46° C.

Scheme 1. Synthesis of 1-(4-methoxyphenyl)-
12-heptyl-1,12-dicarba-closo-dodecaborane

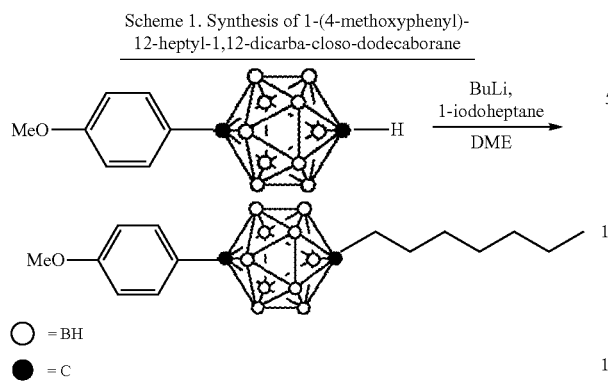

$^1$H NMR (CDCl$_3$): δ 0.87 (t, 3H, CH$_3$), 1.08-1.28 (m, 10H, 5×CH$_2$), 1.64 (m, 2H, C$_{carborane}$—CH$_2$), 1.85-3.0 (br. m, 10H, BH), 3.74 (s, 3H, OCH$_3$), 6.67 (d, 2H, arom., J=9.0 Hz), 7.11 (d, 2H, arom., J=9.0 Hz). $^{13}$C NMR (CDCl$_3$): δ 14.21, 22.73, 29.02, 29.24, 29.67, 31.82, 38.05, 55.39, 80.92, 113.36, 128.49, 128.97, 159.61. Accurate mass HRMS (EI+): m/z calcd. For C$_{16}$H$_{32}$B$_{10}$O (M)$^+$ 348.3465, found 348.3461.

Example 2

To a solution of 1-(4-methoxyphenyl)-1,12-dicarba-closo-dodecaborane (Endo Y et al. *Chemistry & Biology*, 2001, 8, 341-355) (500 mg, 10 mmol) in anhydrous dimethoxyethane DME (100 mL) was added n-butyllithium (4.8 mL, 12 mmol, 2.5 M solution in hexanes) at 0° C. The reaction mixture was stirred at room temperature for 1.5 h. A quantity of 1.83 mL (13 mmol) 1-heptanal was added at 0° C. Following stirring at room temperature overnight, the reaction mixture was carefully poured into 150 mL of 1 M HCl and extracted with ethyl acetate. The organic phase was washed with brine and dried over MgSO$_4$. The solvents were evaporated and the residue purified by column chromatography (hexanes/EtOAc, 19/1, v/v, R$_f$: 0.43) to yield 3.0 g (82%) of a white solid which had a melting point of 104-105° C.

Scheme 2. Synthesis of (*RS*)-1-[1-(4-methoxyphenyl)-
1,12-dicarba-*closo*-dodecaborane-12-yl]heptane-1-ol

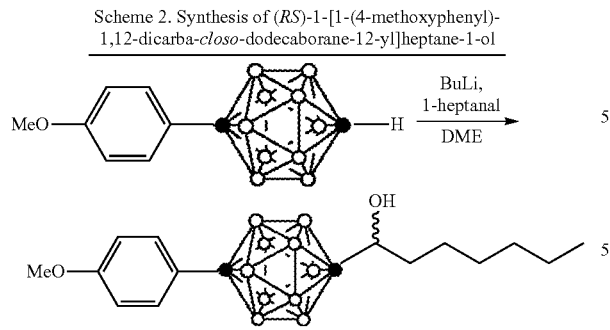

$^1$H NMR (CDCl$_3$): δ 0.88 (t, 3H, CH$_3$), 1.15-1.30 (m, 8H, 4×CH$_2$), 1.38-1.47 (m, 2H, CH$_2$), 1.59 (br.s, 1H, OH), 1.85-3.0 (br. m, 10H, BH), 3.47 (m, 1H, CH), 3.74 (s, 3H, OCH$_3$), 6.68 (d, 2H, arom., J=9.0 Hz), 7.12 (d, 2H, arom., J=9.0 Hz). $^{13}$C NMR (CDCl$_3$): δ 14.20, 22.71, 26.59, 28.98, 31.83, 36.92, 55.39, 73.10, 83.53, 86.36, 113.41, 128.43, 128.84, 159.73. Accurate mass HRMS (EI+): m/z calcd for C$_{16}$H$_{32}$B$_{10}$O$_2$(M)$^+$ 364.3414, found 364.3423.

Example 3

For the synthesis (RS)-1-[1-(4-methoxyphenyl)-1,12-dicarba-closo-dodecaborane-12-yl]butane-1-ol, the procedure and conditions described for the synthesis of (RS)-1-[1-(4-methoxyphenyl)-1,12-dicarba-closo-dodecaborane-12-yl] heptane-1-ol were adapted using 500 mg (2 mmol) 1-(4-methoxyphenyl)-1,12-dicarba-closo-dodecaborane (Endo Y et al. *Chemistry & Biology*, 2001, 8, 341-355) as the starting material.

Scheme 3. Synthesis of (*RS*)-1-[1-(4-methoxyphenyl)-1-12-dicarba-closo-
dodecaborane-12-yl]butane-1-ol

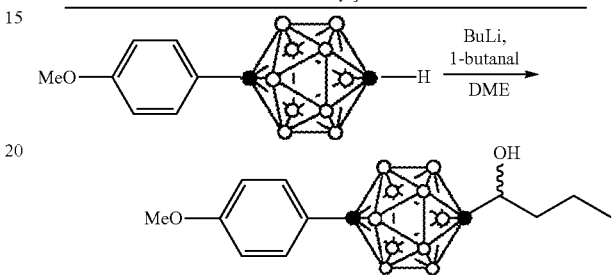

Yield: 500 mg (78%, white solid), R$_f$: 0.33 (hexanes/EtOAc, 19/1, v/v), m.p.: 96-97° C. $^1$H NMR (CDCl$_3$): δ 0.87 (t, 3H, CH$_3$), 1.16-1.27 (m, 4H, 2×CH$_2$), 1.35-1.39 (m, 2H, CH$_2$), 1.45-152 (m, 2H, CH$_2$), 1.59 (br. s, 1H, OH), 1.85-3.0 (br. m, 10H, BH), 3.49 (m, 1H, CH), 3.74 (s, 3H, OCH$_3$), 6.68 (d, 2H, arom., J=9.0 Hz), 7.12 (d, 2H, arom., J=9.0 Hz). $^{13}$C NMR (CDCl$_3$): δ 13.75, 19.82, 38.94, 55.40, 72.84, 83.54, 86.34, 113.42, 128.43, 128.84, 159.73. Accurate mass HRMS (EI+): m/z calcd for C$_{13}$H$_{26}$B$_{10}$O$_2$(M)$^+$ 322.2943, found 322.2929.

Example 4

For the synthesis of (RS)-1-[1-(4-methoxyphenyl)-1,12-dicarba-closo-dodecaborane-12-yl]-6-methylheptane-1-ol, the procedure and conditions described for the synthesis of (RS)-1-[1-(4-methoxyphenyl)-1,12-dicarba-closo-dodecaborane-12-yl]heptane-1-ol were adapted using 1 g (4 mmol) 1-(4-methoxyphenyl)-1,12-dicarba-closo-dodecaborane (Endo Y et al. *Chemistry & Biology*, 2001, 8, 341-355) and 0.75 g (5.85 mmol) of 6-methylheptanal (Kuhnke J & Bohlman F., *Tetrahedron Lett.* 1985, 26, 3955-3958) as the starting materials.

Scheme 4: Synthesis of (*RS*)-1-[1-(4-methoxyphenyl)-1,
12-dicarba-*closo*-dodecaborane-12-yl]-6-methylheptane-1-ol

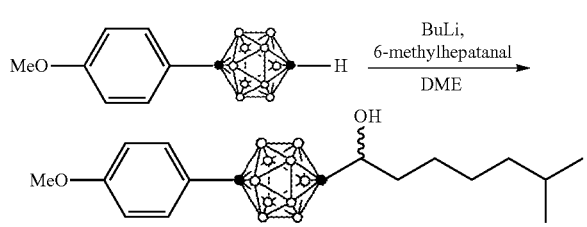

Yield: 1.16 mg (77%, white solid), R$_f$: 0.49 (hexanes/EtOAc, 19/1, v/v), m.p.: 95-96° C. $^1$H NMR (CDCl$_3$): δ 0.85 (s, 3H, CH$_3$), 0.86 (s, 3H, CH$_3$), 1.11-1.28 (m, 6H, 3×CH$_2$), 1.39-1.44 (m, 2H, CH$_2$), 1.47-1.53 (m, 1H, CH), 1.45-152 (m, 2H, CH$_2$), 1.58 (br. s, 1H, OH), 1.85-3.0 (br. m, 10H, BH), 3.47 (m, 1H, CH), 3.74 (s, 3H, OCH$_3$), 6.68 (d, 2H, arom., J=9.0 Hz), 7.12 (d, 2H, arom., J=9.0 Hz). $^{13}$C NMR (CDCl$_3$): δ 22.71, 22.78, 26.89, 27.08, 28.04, 36.94, 38.95, 55.40, 73.10, 83.54, 86.39, 113.42, 128.43, 128.84, 159.73. Accurate mass HRMS (EI+): m/z calcd for C$_{17}$H$_{34}$B$_{10}$O$_2$ (M)$^+$ 378.3571, found 378.3576.

Example 5

For the synthesis of (RS)-1-[1-(4-methoxyphenyl)-1,12-dicarba-closo-dodecaborane-12-yl]-3-phenylpropan-1-ol, the procedure and conditions described for the synthesis of (RS)-1-[1-(4-Methoxyphenyl)-1,12-dicarba-closo-dodecaborane-12-yl]heptane-1-ol were adapted using 250 mg (1 mmol) 1-(4-methoxyphenyl)-1,12-dicarba-closo-dodecaborane (Endo Y et al. *Chemistry & Biology*, 2001, 8, 341-355) and 0.17 g (1.5 mmol) of 3-phenylheptanal as the starting materials.

Scheme 5: Synthesis of (RS)-1-[1-(4-methoxyphenyl)-1, 12-dicarba-*closo*-dodecaborane-12-yl]-3-phenylpropan-1-ol

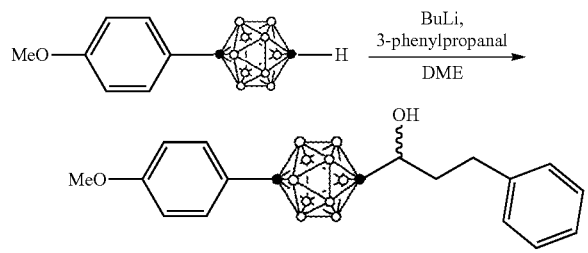

Yield: 344 mg (90%, white solid), R$_f$: 0.27 (hexanes/EtOAc, 19/1, v/v), m.p.: 123-124° C. $^1$H NMR (CDCl$_3$): δ 01.49-1.77 (m, 2H, CH$_2$), 1.69 (br. s, 1H, OH), 1.85-3.0 (br. m, 10H, BH), 2.51-2.83 (m, 2H, CH$_2$), 3.48 (m, 1H, CH), 3.74 (s, 3H, OCH$_3$), 6.68 (d, 2H, arom., J=9.0 Hz), 7.11 (d, 2H, arom., J=9.0 Hz), 7.14 (d, 2H, arom.), 7.20 (t, 1H, arom.), 7.28 (t, 2H, arom.). $^{13}$C NMR (CDCl$_3$): δ 32.69, 38.29, 55.39, 72.31, 83.64, 86.02, 113.42, 126.19, 128.41, 128.52, 128.61, 128.77, 141.15, 159.74. Accurate mass HRMS (EI+): m/z calcd for C$_{18}$H$_{28}$B$_{10}$O$_2$(M)$^+$384.3102, found 38.3101.

Example 6

For the synthesis of (RS)-(2,3-dihydro-1H-inden-5-yl)-[1-(4-methoxyphenyl)-1,12-dicarba-closo-dodecaborane-12-yl]methanol, the procedure and conditions described for the synthesis of (RS)-1-[1-(4-Methoxyphenyl)-1,12-dicarba-closo-dodecaborane-12-yl]heptane-1-ol were adapted using 450 mg (1.8 mmol) 1-(4-methoxyphenyl)-1,12-dicarba-closo-dodecaborane (Endo Y et al. *Chemistry & Biology*, 2001, 8, 341-355) and 100 g (0.69 mmol) of 5-formylindane as the starting materials. Subsequent to the reaction, excess 1-(4-methoxyphenyl)-1,12-dicarba-closo-dodecaborane was initially recovered by column chromatography using hexanes only.

Scheme 6:
Synthesis of (RS)-(2,3-dihydro-1H-inden-5-yl)-[1-(4-methoxyphenyl)-1, 12-dicarba-*closo*-dodecaborane-12-yl]methanol

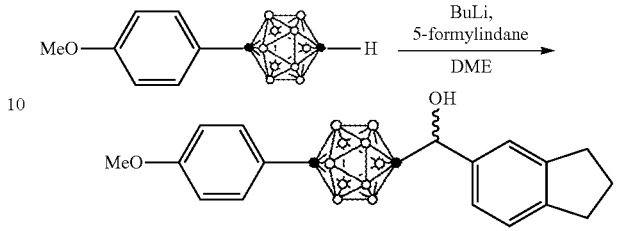

Yield: 240 mg (79%, white solid), R$_f$: 0.28 (hexanes/EtOAc, 19/1, v/v), m.p.: 123-124° C. $^1$H NMR (CDCl$_3$): δ 1.85-3.0 (br. m, 10H, BH), 2.06-2.10 (m, 3H, CH$_2$, OH), 2.89 (m, 4H, 2×CH$_2$), 3.74 (s, 3H, OCH$_3$), 4.46 (s, 1H, CH), 6.66 (d, 2H, arom., J=9.0 Hz), 6.92 (d, 1H, arom.), 7.03 (s, 1H, arom.), 7.09 (d, 2H, arom., J=9.0 Hz), 7.15 (d, 2H, arom.). $^{13}$C NMR (CDCl$_3$): δ 25.56, 32.77, 32.95, 55.39, 76.11, 83.65, 85.84, 113.39, 122.74, 123.95, 124.92, 128.41, 128.86, 138.24, 144.29, 144.95, 159.71. Accurate mass HRMS (EI+): m/z calcd for C$_{19}$H$_{28}$B$_{10}$O$_2$(M)$^+$396.3102, found 396.3096.

Example 7

Pyridinium chlorochromate (PCC, 2.0 g, 9.34 mmol) was suspended in anhydrous DCM (50 mL). A solution of (RS)-1-[1-(4-methoxyphenyl)-1,12-dicarba-closo-dodecaborane-12-yl]heptane-1-ol (1.7 g, 4.67 mmol) in anhydrous DCM (15 mL) was then added to give a dark reaction mixture, which was stirred at room temperature overnight. Diethylether (60 mL) was added and then molecular sieve followed by stirring for 1 h. The supernatant was decanted and the insoluble residue was washed with dry ether (3×20 mL). The combined organic phases were passed through a short column of florisil followed by evaporation. The residue was purified by silica gel column chromatography (hexanes, R$_f$: 0.13) to yield 1.6 g (95%) of a white wax-like solid which had a melting point of 36-37° C.

Scheme 7. Synthesis of 1-[1-(4-methoxyphenyl)-1, 12-dicarba-*closo*-dodecaborane-12-yl]heptane-1-one.

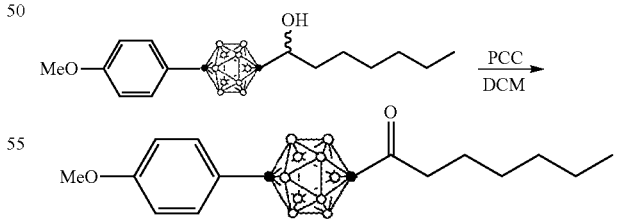

$^1$H NMR (CDCl$_3$): δ 0.87 (t, 3H, CH$_3$), 1.14-1.46 (m, 8H, 4×CH$_2$), 1.85-3.0 (br. m, 10H, BH), 2.39 (m, 2H, C(O)—CH$_2$), 3.74 (s, 3H, OCH$_3$), 6.69 (d, 2H, arom., J=9.0 Hz), 7.10 (d, 2H, arom., J=8.9 Hz). $^{13}$C NMR (CDCl$_3$): δ 14.14, 22.58, 23.60, 28.51, 31.60, 39.39, 55.41, 83.75, 85.64, 113.50, 128.28, 128.73, 159.92, 195.48. Accurate mass HRMS (EI+): m/z calcd for C$_{16}$H$_{30}$B$_{10}$O$_2$(M)$^+$ 362.3257, found 362.3254.

Example 8

Borane-tetrahydrofuran complex (16.5 mL, 16.5 mmol, 1.0 M solution in THF, stabilized with 0.005 M N-isopropyl-N-methyl-tert-butylamine (NIMBA)) followed by (S)-2-methyl-CBS-oxazaborolidine [(S)-MeCBS] (1.65 mL, 1.65 mmol, 1.0 M solution in toluene) were added to 15 mL anhydrous THF. The reaction mixture was stirred at room temperature for 10 minutes and 1-[1-(4-methoxyphenyl)-1,12-dicarba-closo-dodecaborane-12-yl]heptane-1-one (600 mg, 1.65 mmol) in 15 mL of anhydrous THF was added slowly over a period of 2 h at 25° C. The reaction mixture was stirred for additional 6 h at room temperature and then carefully quenched by addition of 2.0 M HCl (30 mL) in small portions to control $H_2$ development. Diethyl ether (50 mL) was added and the organic phase was washed brine and saturated $NaHCO_3$. The organic phase was dried over $MgSO_4$, filtered, and evaporated. The residue was purified by silica gel column chromatography (hexanes/EtOAc, 19/1, v/v) to yield a white solid. Based on chiral HPLC (CHIRALPAK IB-3 [Chiral Technologies, INC.], hexanes/DCM [9/1], 1 mL flow rate), and analysis of the $^1$H NMR spectrum of the corresponding Mosher ester, the enantiomeric excess (ee) was estimated to be >85%. The absolute configuration was determined by analysis of the $^1$H NMR spectrum of the corresponding Mosher ester.

Scheme 8. Synthesis of (R)-1-[1-(4-hydoxyphenyl)-1,12-dicarba-closo-dodecaborane-12-yl]heptane-1-ol.

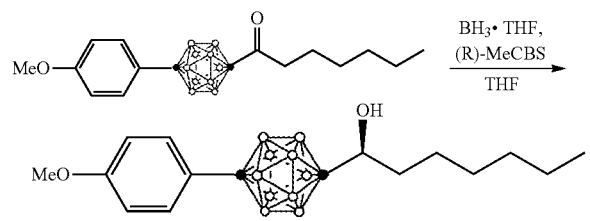

Yield: 440 mg (73%), $R_f$: 0.43 (hexanes/EtOAc, 19/1, v/v), m.p.: 95-96° C., $[\alpha]_D^{20°C.}=+27°$ (0.1, DCM). $^1$H NMR (CDCl$_3$): δ 0.87 (t, 3H, CH$_3$), 1.15-1.31 (m, 8H, 4×CH$_2$), 1.38-1.48 (m, 2H, CH$_2$), 1.58 (br. s, 1H, OH), 1.85-3.0 (br. m, 10H, BH), 3.47 (m, 1H, CH), 3.74 (s, 3H, OCH$_3$), 6.68 (d, 2H, arom., J=9.0 Hz), 7.12 (d, 2H, arom., J=9.0 Hz). $^{13}$C NMR (CDCl$_3$): δ 14.20, 22.72, 26.60, 28.98, 31.83, 36.92, 55.40, 73.10, 83.53, 86.39, 113.42, 128.43, 128.85, 159.73. Accurate mass HRMS (EI+): m/z calcd for $C_{16}H_{32}B_{10}O_2$ (M)$^+$ 364.3414, found 364.3417.

Example 9

For the synthesis of (R)-1-[1-(4-methoxyphenyl)-1,12-dicarba-closo-dodecaborane-12-yl]heptane-1-ol, the procedure and conditions described for the synthesis of (s)-1-[1-(4-methoxyphenyl)-1,12-dicarba-closo-dodecaborane-12-yl]heptane-1-ol were adapted using 500 mg (1.38 mmol) of 1-[1-(4-methoxyphenyl)-1,12-dicarba-closo-dodecaborane-12-yl]heptane-1-one and 1.38 mL (1.38 mmol, 1.0 M solution in toluene) of (R)-MeCBS. The residue was purified by silica gel column chromatography (hexanes/EtOAc, 19/1, v/v) to yield a white solid. Based on chiral HPLC (CHIRALPAK IB-3 [Chiral Technologies, INC.], hexanes/DCM [9/1], 1 mL flow rate), the enantiomeric excess (ee) was estimated to be >85%. The assignment of the absolute configuration was derived from the analysis of the $^1$H-NMR spectrum of the Mosher ester of (S)-1-[1-(4-methoxyphenyl)-1,12-dicarba-closo-dodecaborane-12-yl]heptane-1-ol.

Scheme 9. Synthesis of (R)-1-[1-(4-methoxyphenyl)-1,12-dicarba-closo-dodecaborane-12-yl]heptane-1-ol

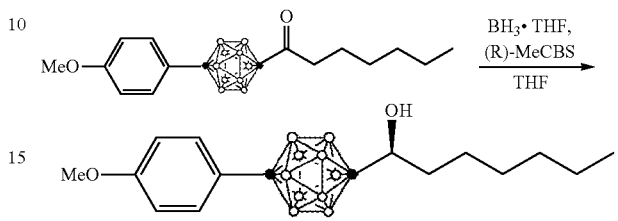

Yield: 400 mg (80%), $R_f$: 0.43 (hexanes/EtOAc, 19/1, v/v), m.p.: 95-96° C., $[\alpha]_D^{20°C.}=-24°$ (0.1, DCM). $^1$H NMR (CDCl$_3$): δ 0.87 (t, 3H, CH$_3$), 1.15-1.31 (m, 8H, 4×CH$_2$), 1.38-1.47 (m, 2H, CH$_2$), 1.57 (br. s, 1H, OH), 1.85-3.0 (br. m, 10H, BH), 3.47 (m, 1H, CH), 3.74 (s, 3H, OCH$_3$), 6.68 (d, 2H, arom., J=9.0 Hz), 7.12 (d, 2H, arom., J=9.0 Hz). $^{13}$C NMR (CDCl$_3$): δ 14.20, 22.72, 26.60, 28.99, 31.83, 36.92, 55.40, 73.10, 83.54, 86.39, 113.42, 128.43, 128.85, 159.73. Accurate mass HRMS (EI+): m/z calcd for $C_{16}H_{32}B_{10}O_2$ (M)$^+$ 364.3414, found 364.3406.

Example 10

To a solution of 1-(4-methoxyphenyl)-12-heptyl-1,12-dicarba-closo-dodecaborane (600 mg, 1.72 mmol) in anhydrous DCM (40 mL) was added boron tribromide (3.4 mL, 3.4 mmol), 1 M solution in DCM at 0° C. The reaction mixture was stirred at room temperature overnight, poured carefully into ice-cold 1 M HCl (60 mL) and extracted with DCM. The organic phase was washed with a 10% sodium thiosulfate solution and brine and dried over MgSO$_4$. The solvents were evaporated and the residue purified by silica gel column chromatography (hexanes/EtOAc, 9/1, v/v) to yield a white solid. Further purification can be achieved by recrystallization from pentane or hexanes (−20° C.).

Scheme 10.
Synthesis of 1-(4-hydroxyphenyl)-12-heptyl-1,12-dicarba-closo-dodecaborane.

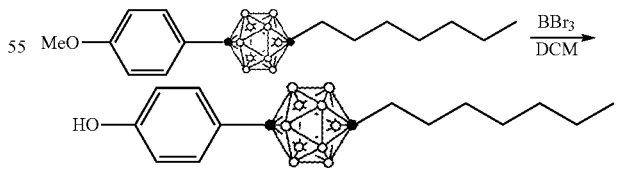

Yield: 380 mg (66%), $R_f$: 0.36 (hexanes/EtOAc, 9/1, v/v), m.p.: 114-115° C. $^1$H NMR (CDCl$_3$): δ 0.87 (t, 3H, CH$_3$), 1.08-1.29 (m, 10H, 5×CH$_2$), 1.64 (m, 2H, C$_{carborane}$—CH$_2$), 1.85-3.0 (br. m, 10H, BH), 4.68 (br. s, 1H, OH), 6.60 (d, 2H, arom., J=8.8 Hz), 7.07 (d, 2H, arom., J=8.8 Hz). $^{13}$C NMR (CDCl$_3$): δ 14.20, 22.73, 29.02, 29.23, 29.67, 31.87, 38.04, 80.82, 80.98, 81.21, 114.83, 128.76, 129.30, 155.59. Accurate mass HRMS (ESI): m/z calcd for $C_{15}H_{29}B_{10}O$ (M−1)⁻ 333.3216, found 333.3213.

Example 11

To a solution of (RS)-1-[1-(4-methoxyphenyl)-1,12-dicarba-closo-dodecaborane-12-yl]heptane-1-ol (570 mg, 1.57 mmol) in anhydrous DCM (40 mL) was added boron tribromide (4.7 mL, 4.7 mmol, 1 M solution in DCM) at 0° C. The reaction mixture was stirred at room temperature overnight, poured carefully into ice-cold 1 M HCl (60 mL) and extracted with DCM. The organic phase was washed with a 10% sodium thiosulfate solution and brine and dried over $MgSO_4$. The solvents were evaporated and the residue purified by silica gel column chromatography (hexanes/EtOAc, 9/1, v/v) to yield a white solid. Further purification can be achieved by recrystallization from hexanes/i-propanol [24:1] and washing the obtained residue with ice-cold pentane.

Scheme 11.
Synthesis of (RS)-1-[1-(4-hydoxyphenyl)-1,12-dicarba-closo-dodecaborane-12-yl]heptane-1-ol.

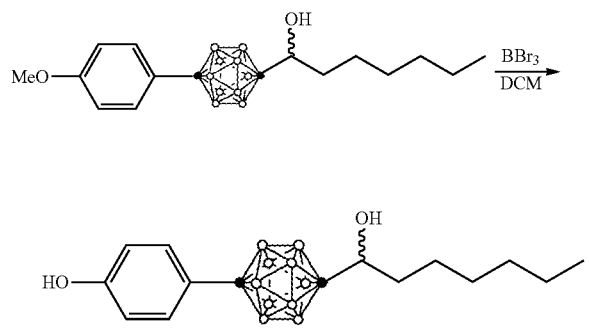

Yield: 400 mg (73%), $R_f$: 0.23 (hexanes/EtOAc, 9/1, v/v), m.p.: 129-130° C. ¹H NMR (CDCl₃): δ 0.87 (t, 3H, CH₃), 1.14-1.30 (m, 8H, 4×CH₂), 1.38-1.45 (m, 2H, CH₂), 1.62-1.63 (m, ~2H, OH & H₂O), 1.85-3.0 (br. m, 10H, BH), 3.46 (m, 1H, CH), 4.96 (br. s, 1H, OH), 6.61 (d, 2H, arom., J=8.8 Hz), 7.07 (d, 2H, arom., J=8.9 Hz). ¹³C NMR (CDCl₃): δ 14.19, 22.71, 26.58, 28.97, 31.82, 36.91, 73.14, 83.57, 86.37, 114.90, 128.68, 129.06, 155.82. Accurate mass HRMS (ESI): m/z calcd for $C_{15}H_{31}B_{10}O_2$(M+1)⁻ 351.3329, found 351.3322.

Example 12

The procedure and conditions described for the synthesis of (RS)-1-[1-(4-hydroxyphenyl)-1,12-dicarba-closo-dodecaborane-12-yl]heptane-1-ol were adapted using 450 mg (1.4 mmol) (RS)-1-[1-(4-methoxyphenyl)-1,12-dicarba-closo-dodecaborane-12-yl]butane-1-ol as the starting material. Purification of the products is carried out by silica gel column chromatography (hexanes/EtOAc, 9/1, v/v) to yield a white solid. Further purification can be achieved by recrystallization from hexanes/i-propanol [24:1] and washing the obtained residue with ice-cold pentane.

Scheme 12. Synthesis of (RS)-1-[1-(4-methoxyphenyl)-1, 12-dicarba-closo-dodecaborane-12-yl]butane-1-ol.

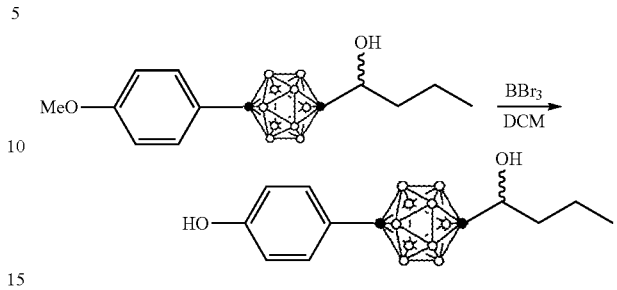

Yield: 265 mg (62%), $R_f$: 0.22 (hexanes/EtOAc, 9/1, v/v), m.p.: 184-185° C. ¹H NMR (CDCl₃): δ 0.87 (t, 3H, CH₃), 1.15-1.26 (m, 2H, CH₂), 1.33-1.51 (m, 2H, CH₂), 1.55 (br.s, ~2H, OH & H₂O), 1.85-3.0 (br. m, 10H, BH), 3.48 (m, 1H, CH), 4.69 (br. s, ~1H, OH), 6.61 (d, 2H, arom., J=8.8 Hz), 7.07 (d, 2H, arom., J=8.8 Hz). ¹³C NMR (CDCl₃): δ 13.75, 19.82, 38.95, 72.86, 83.41, 86.39, 114.90, 128.71, 129.15, 155.75. Accurate mass HRMS (ESI): m/z calcd for $C_{12}H_{23}B_{10}O_2$(M−1)⁻ 307.2701, found 307.2700.

Example 13

The procedure and conditions described for the synthesis of (RS)-1-[1-(4-hydroxyphenyl)-1,12-dicarba-closo-dodecaborane-12-yl]heptane-1-ol were adapted using 550 mg (1.46 mmol) (RS)-1-[1-(4-methoxyphenyl)-1,12-dicarba-closo-dodecaborane-12-yl]-6-methylheptane-1-ol as the starting material. Purification of the products is carried out by silica gel column chromatography (hexanes/EtOAc, 9/1, v/v) to yield a white solid. Further purification can be achieved by recrystallization from hexanes/i-propanol [24:1] and washing the obtained residue with ice-cold pentane.

Scheme 13. Synthesis of (RS)-1-[1-(4-hydroxyphenyl)-1, 12-dicarba-closo-dodecaborane-12-yl]-6-methylheptane-1-ol.

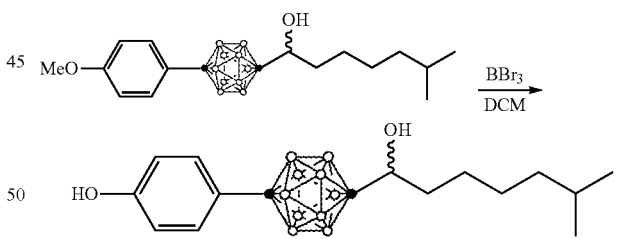

Yield: 340 mg (72%), $R_f$: 0.23 (hexanes/EtOAc, 9/1, v/v), m.p.: 120-121° C. ¹H NMR (CDCl₃): δ 0.84 (s, 3H, CH₃), S 0.85 (s, 3H, CH₃), 1.10-1.28 (m, 6H, 3×CH₂), 1.38-1.45 (m, 2H, CH₂), 1.46-1.52 (m, 1H, CH), 1.61 (br.s, ~2H, OH & H₂O), 1.85-3.0 (br. m, 10H, BH), 3.47 (m, 1H, CH), 4.88 (br. s, ~1H, OH), 6.61 (d, 2H, arom., J=8.8 Hz), 7.07 (d, 2H, arom., J=8.8 Hz). ¹³C NMR (CDCl₃): δ 22.71, 22.78, 26.88, 27.07, 28.04, 36.93, 38.94, 73.13, 83.33, 86.38, 114.90, 128.69, 129.09, 155.80. Accurate mass HRMS (ESI): m/z calcd for $C_{16}H_{31}B_{10}O_2$(M−1)⁻ 363.3322, found 363.3331.

Example 14

The procedure and conditions described for the synthesis of (RS)-1-[1-(4-hydroxyphenyl)-1,12-dicarba-closo-dodecaborane-12-yl]heptane-1-ol were adapted using 250 mg (0.65 mmol) (RS)-1-[1-(4-methoxyphenyl)-1,12-dicarba-closo-dodecaborane-12-yl]-3-phenylpropan-1-ol as the starting material. Purification of the products is carried out by silica gel column chromatography (hexanes/EtOAc, 9/1, v/v) to yield a white solid. Further purification can be achieved by recrystallization from hexanes/i-propanol [24:1] and washing the obtained residue with ice-cold pentane.

Scheme 14. Synthesis of (RS)-1-[1-(4-hydroxyphenyl)-1, 12-dicarba-*closo*-dodecaborane-12-yl]-3-phenylpropan-1-ol

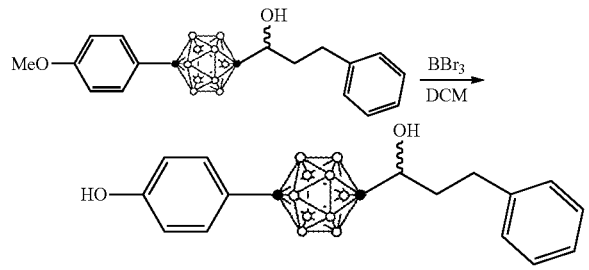

Yield: 200 mg (83%), $R_f$: 0.15 (hexanes/EtOAc, 9/1, v/v), m.p.: 135-136° C. $^1$H NMR (CDCl$_3$): δ 01.49-1.77 (m, 2H, CH$_2$), 1.70 (br. s, ~1H, OH), 1.85-3.0 (br. m, 10H, BH), 2.50-2.78 (m, 2H, CH$_2$), 3.48 (m, 1H, CH), 4.81 (br. s, 1H, OH), 6.60 (d, 2H, arom., J=8.8 Hz), 7.06 (d, 2H, arom., J=8.8 Hz), 7.14 (d, 2H, arom.), 7.19 (t, 1H, arom.), 7.28 (t, 2H, arom.). $^{13}$C NMR (CDCl$_3$): δ 32.68, 38.29, 72.35, 83.56, 86.01, 126.20, 128.52, 128.61, 128.68, 129.04, 141.12, 155.78. Accurate mass HRMS (ESI): m/z calcd for C$_{17}$H$_{25}$B$_{10}$O$_2$(M−1)$^-$ 369.2852, found 369.2851.

Example 15

The procedure and conditions described for the synthesis of (RS)-1-[1-(4-hydroxyphenyl)-1,12-dicarba-closo-dodecaborane-12-yl]heptane-1-ol were adapted using 280 mg (0.63 mmol) (RS)-(2,3-dihydro-1H-inden-5-yl)-[1-(4-methoxyphenyl)-1,12-dicarba-closo-dodecaborane-12-yl]methanol as the starting material. Purification of the products is carried out by silica gel column chromatography (hexanes/EtOAc, 9/1, v/v) to yield a white solid. Further purification can be achieved by refluxing a suspension of the product in hexanes/i-propanol [24:1] and, after cooling the suspension to 0° C., washing the obtained residue with ice-cold pentane.

Scheme 15: Synthesis of (RS)-(2,3-dihyrdo-1H-inden-5-yl)-[1-(4-hydroxyphenyl)-1,12-dicarba-*closo*-dodecaborane-12-yl]methanol

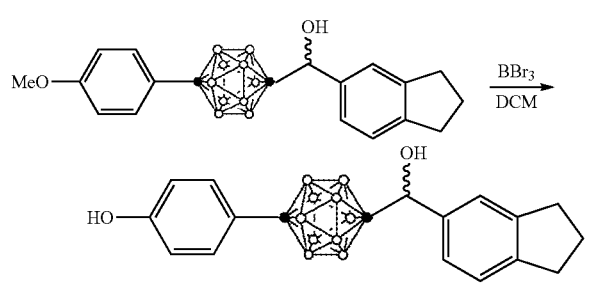

Yield: 240 mg (89%), $R_f$: 0.19 (hexanes/EtOAc, 9/1, v/v), m.p.: 231° C. (decomp.). $^1$H NMR (Acetone-d$_6$): δ 1.9-3.0 (br. m, 10H, BH), 2.06 (m, ~2H, CH$_2$), 2.88 (m, ~4H, 2×CH$_2$), 4.68 (s, H, OH), 4.99 (m, 1H, CH), 6.66 (d, 2H, arom., J=8.6 Hz), 6.97 (d, 1H, arom.), 7.05 (d, 2H, arom., J=8.9 Hz), 7.08 (s, 1H, arom.), 7.13 (d, 2H, arom.), 8.51 (s, H, OH). $^{13}$C NMR (Acetone-d$_6$): δ 26.41, 33.09, 33.31, 75.96, 84.58, 88.01, 115.65, 123.59, 124.21, 125.86, 128.30, 129.09, 140.63, 144.24, 144.71, 158.58. Accurate mass HRMS (ESI): m/z calcd for C$_{18}$H$_{25}$B$_{10}$O$_2$ (M−1)$^-$ 381.2852, found 381.2855.

Example 16

To a solution of 1-[1-(4-methoxyphenyl)-1,12-dicarba-closo-dodecaborane-12-yl]heptane-1-one (630 mg, 1.74 mmol) in anhydrous DCM (40 mL) was added boron tribromide (5.2 mL, 5.2 mmol, 1 M solution in DCM) at 0° C. The reaction mixture was stirred at room temperature overnight, poured carefully into ice-cold 1 M HCl (60 mL) and extracted with DCM. The organic phase was washed with a 10% sodium thiosulfate solution and brine and dried over MgSO$_4$. The solvents were evaporated and the residue purified by silica gel column chromatography (hexanes/EtOAc, 9/1, v/v) to yield a white solid. Further purification can be achieved by recrystallization from pentane or hexanes (−20° C.).

Scheme 16. Synthesis of 1-[1-(4-hydroxyphenyl)-1,12-dicarba-*closo*-dodecaborane-12-yl]heptane-1-one.

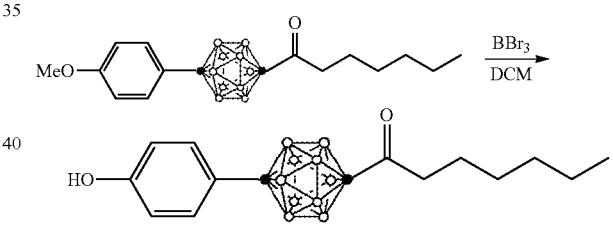

Yield: 520 mg (86%), $R_f$: 0.31 (hexanes/EtOAc, 9/1, v/v), m.p.: 79-80° C. $^1$H NMR (CDCl$_3$): δ 0.86 (t, 3H, CH$_3$), 1.12-1.27 (m, 6H, 3×CH$_2$), 1.39-1.46 (m, 2H, CH$_2$), 1.55-3.40 (br. m, 10H, BH), 2.39 (t, 2H, C(O)—CH$_2$), 5.11 (br. s, 1H, OH), 6.62 (d, 2H, arom., J=8.7 Hz), 7.05 (d, 2H, arom., J=8.9 Hz). $^{13}$C NMR (CDCl$_3$): δ 14.09, 22.52, 23.53, 28.44, 31.54, 39.40, 83.61, 85.83, 114.95, 128.49, 128.87, 155.99, 195.87. Accurate mass HRMS (ESI): m/z calcd for C$_{15}$H$_{27}$B$_{10}$O$_2$(M−1)$^-$ 347.3001, found 347.3014.

Example 17

The procedure and conditions described for the synthesis of (RS)-1-[1-(4-methoxyphenyl)-1,12-dicarba-closo-dodecaborane-12-yl]heptane-1-ol were adapted using 300 mg (0.825 mmol) (S)-1-[1-(4-methoxyphenyl)-1,12-dicarba-closo-dodecaborane-12-yl]heptane-1-ol as the starting material. Purification of the products is carried out by silica gel column chromatography (hexanes/EtOAc, 9/1, v/v) to yield a white solid. Further purification can be achieved by refluxing a suspension of the product in hexanes/i-propanol [24:1] and, after cooling the suspension to 0° C., washing the obtained residue with ice-cold pentane. The enantiomeric excess (ee) was estimated to be >85% according to analysis of the ¹H-NMR spectrum of the corresponding Mosher ester. The absolute configuration was determined by analysis of the ¹H-NMR spectrum of the corresponding Mosher ester.

Scheme 17: Synthesis (S)-1-[1-(4-hydoxyphenyl)-1,12-dicarba-*closo*-dodecaborane-12-yl]heptane-1-ol

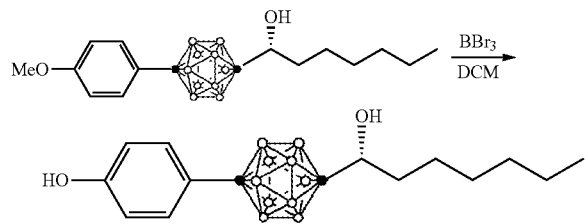

Yield: 220 mg (76%), R$_f$: 0.23 (hexanes/EtOAc, 9/1, v/v), m.p.: 120-121° C., $[\alpha]_D^{20\ °C}$=+23° (0.1, DCM). ¹H NMR (CDCl$_3$): δ 0.87 (t, 3H, CH$_3$), 1.15-1.30 (m, 8H, 4×CH$_2$), 1.39-1.45 (m, 2H, CH$_2$), 1.66-1.71 (m, 2H, OH & H$_2$O), 1.85-3.0 (br. m, 10H, BH), 3.46 (m, 1H, CH), 5.08 (br. s, 1H, OH), 6.61 (d, 2H, arom., J=8.8 Hz), 7.07 (d, 2H, arom., J=8.9 Hz). ¹³C NMR (CDCl$_3$): δ 14.19, 22.70, 26.58, 28.97, 31.81, 36.90, 73.16, 83.49, 86.33, 114.90, 128.67, 129.03, 155.84. Accurate mass HRMS (ESI): m/z calcd for C$_{15}$H$_{29}$B$_{10}$O$_2$ (M−1)⁻ 349.3165, found 349.3162.

Example 18

The procedure and conditions described for the synthesis of (RS)-1-[1-(4-hydroxyphenyl)-1,12-dicarba-closo-dodecaborane-12-yl]heptane-1-ol were adapted using 300 mg (0.825 mmol) (R)-1-[1-(4-methoxyphenyl)-1,12-dicarba-closo-dodecaborane-12-yl]heptane-1-ol as the starting material. Purification of the products is carried out by silica gel column chromatography (hexanes/EtOAc, 9/1, v/v) to yield a white solid. Further purification can be achieved by refluxing a suspension of the product in hexanes/i-propanol [24:1] and, after cooling the suspension to 0° C., washing the obtained residue with ice-cold pentane. The enantiomeric excess (ee) was estimated to be >85% according to analysis of the ¹H-NMR spectrum of the corresponding Mosher ester. The absolute configuration was determined by analysis of the ¹H-NMR spectrum of the corresponding Mosher ester.

Scheme 18: Synthesis (R)-1-[1-(4-hydoxyphenyl)-1,12-dicarba-*closo*-dodecaborane-12-yl]heptane-1-ol

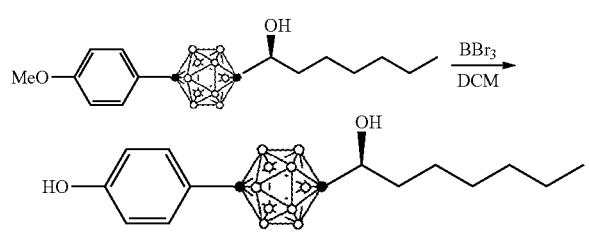

Yield: 180 mg (62%), R$_f$: 0.23 (hexanes/EtOAc, 9/1, v/v), m.p.: 120-121° C., $[\alpha]_D^{20\ °C}$=−28° (0.1, DCM). ¹H NMR (CDCl$_3$): δ 0.87 (t, 3H, CH$_3$), 1.15-1.30 (m, 8H, 4×CH$_2$), 1.39-1.45 (m, 2H, CH$_2$), 1.68-1.76 (m, 2H, OH & H$_2$O), 1.9-3.0 (br. m, 10H, BH), 3.47 (m, 1H, CH), 5.17 (br. s, 1H, OH), 6.61 (d, 2H, arom., J=8.8 Hz), 7.07 (d, 2H, arom., J=8.9 Hz). ¹³C NMR (CDCl$_3$): δ 14.19, 22.70, 26.58, 28.96, 31.81, 36.90, 73.17, 83.50, 86.31, 114.90, 128.67, 129.01, 155.86. Accurate mass HRMS (ESI): m/z calcd for C$_{15}$H$_{29}$B$_{10}$O$_2$(M−1)⁻ 349.3165, found 349.3158.

Example 19

Estrogen receptor beta (ERβ) agonists have the potential to function as tumor suppressors in the treatment of cancers, such as breast, colon, and prostate cancer. Such agents can also be used in the treatment of inflammatory diseases, such as arthritis and inflammatory bowel disease, as well as in some neurodegenerative and psychotropic disorders.

A library of twenty two compounds (Table 2) was synthesized (for example, as described above or using methods derived therefrom), and biologically evaluated in vitro for estrogen receptor beta (ERβ) selective agonist activity. The library of twenty two compounds was synthesized based on reference compounds (Table 1). Within synthesized structures (Table 2), the B and C rings of the endogenous ligand E2 were replaced with a carborane cluster. The hydrophobicity character and the spherical geometry of the carborane can play a role in enhancing the binding affinity of ligands to estrogen receptor.

In addition to the three reference compounds (Table 1) and the library of twenty two synthesized compounds (Table 2), three compounds described by Thirumamagal, B T S et al. (*Bioconj. Chem.* 2006, 17, 114-1150) were also included in the in vitro evaluation of ERβ selective agonist activity (Table 3).

The selectivity and potency of the various compounds was carried out via in vitro testing in ERα and ERβ cell-based reporter assays. The activity of the selected compounds was determined in the cell-based reporter assays in HEK293 cells. The HEK293 cell line was chosen as it does not express endogenous ERα or ERβ at significant levels.

The HEK293 cells were propagated in a monolayer in phenol red-free DMEM supplemented with 10% fetal bovine serum, 2 mM Glutamax and penicillin/streptomycin (Thermo Fisher Scientific, MA, USA) and incubated in a 5% CO$_2$ humidified atmosphere at 37° C. Right before transfection, the growth medium was changed to phenol red-free DMEM supplemented with 4% HyClone Fetal Bovine Serum, Charcoal/Dextran Treated (GE Healthcare Life Sciences, USA) and 2 mM Glutamax (starvation medium). The cells were transfected with the expression vector encoding human full-length ERα or ERβ and with the reporter vector containing 3 repeats of estrogen responsive elements (ERE) followed by the minimal thymidine kinase promoter from the herpes simplex virus in the pGL4 vector (Promega, USA). Luciferase served as a reporter gene. The transfection was carried out in 10 cm dishes (Nunc) in the starvation medium. After 24 hours, the cells were trypsinized, counted and seeded to cell culture treated, white, solid 1536-well plates (Corning Inc., NY, USA) at 1500 cells/well in 4 µl of total media volume. The compounds to be tested were diluted in DMSO and transferred to the cells using an acoustic dispenser Echo 520 (Labcyte). The compounds were tested at least at 12 different concentration points in the range from 10 µM to 100 pM, in triplicates. Luciferase activity was determined after 24 hours of incubation with compounds with Britelite plus luciferase reporter gene assay reagent (Perkin Elmer, USA), according to the manufacturer protocol. The luciferase signal was measured on an Envison multimode plate reader (Perkin Elmer, USA). Data were collected and processed using an in-house built LIMS system ScreenX and GraphPad Prism software. $EC_{50}$ values were calculated using a regression function (dose response, variable slope). The assay description is summarized in Table 4.

The results of the in vitro evaluation of the compounds for estrogen receptor beta (ERβ) selective agonist activity are summarized in Table 5. Experiments on compound 04 indicated it had an $EC_{50}$ at ERα of >5000 nM and an $EC_{50}$ at ERβ of 46 nM, indicating a high ERβ selectivity. Experiments on compound 05 indicated it had an $EC_{50}$ at ERα of >5000 nM and an $EC_{50}$ at ERβ of 64 nM, indicating a high ERβ selectivity.

The results (Table 5) indicated that the active carboranyl compounds of the synthesized library were those where the para-hydrophenyl-ring (A-ring) of E2 was retained to allow for hydrogen bond- and pi-stacking interactions with the receptor. The results further indicated that the active compounds from the synthesized library were those where the D-ring of E2, containing a 17β-hydroxyl group, was replaced with an alkyl- or a 1-hydroxyalkyl group. The latter structural element appeared to be related to selectivity for ERβ.

One promising compound of this library was 1-(4-hydoxyphenyl)-12-(1-hydroxyheptyl)-1,12-dicarba-closo-dodecaborane (06). Evaluation of this compound in a luciferase reporter-based cell assay in human embryonic kidney (HEK) cells (Sedlak, D. et al. *Comb. Chem. High T. Scr.* 2011, 14, 248-266) resulted in an $EC_{50}$ of 5 nM at ERβ and an ERβ-to-ERα agonist ratio of 1,800. For comparison, the standard ERβ selective agonist diarylpropionitrile (DPN) had an $EC_{50}$ of 6.3 nM and an ERβ-to-ERα agonist ratio of 358.

TABLE 1

Reference Compounds.

| Compound Name | Structure |
| --- | --- |
| Estradiol (E2) | 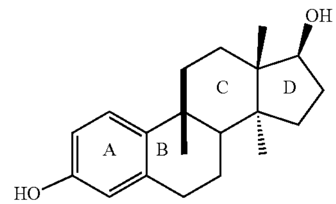 |
| Diarylpropionitrile (DPN) (ERβ selective agonist) | 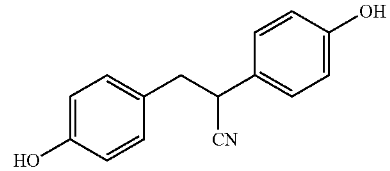 [SMILES: N#CC(Cc1ccc(O)cc1)c1ccc(O)cc1] |
| Propyl pyrazole triol (PPT) (ERα selective agonist) | 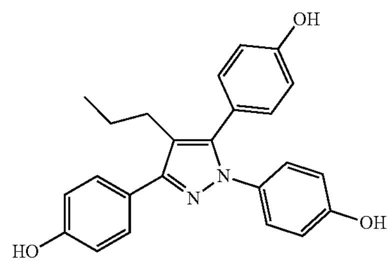 [SMILES: CCCc1c(-c2ccc(O)cc2)nn(-c2ccc(O)cc2)c1-c1ccc(O)cc1] |

TABLE 2

Synthesized library of compounds.

| Compound | Structure |
| --- | --- |
| 04 | 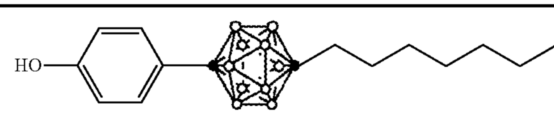 |
| 05 | 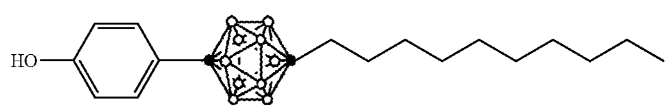 |
| 06 | 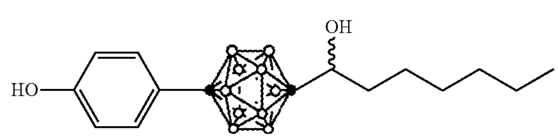 |
| 07 | 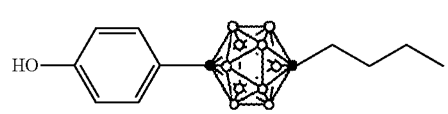 |
| 08 | 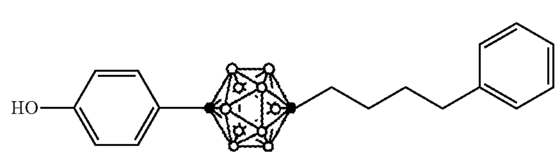 |

TABLE 2-continued

Synthesized library of compounds.

| Compound | Structure |
|---|---|
| 09 | 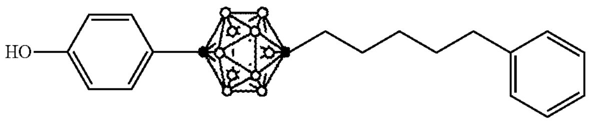 |
| 10 | 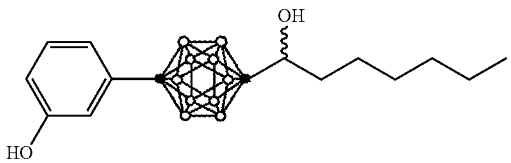 |
| 11 | 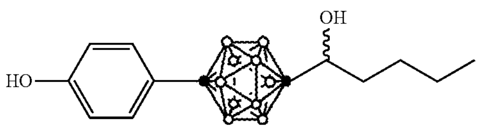 |
| 12 | 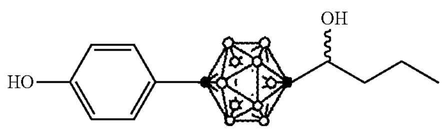 |
| 13 | 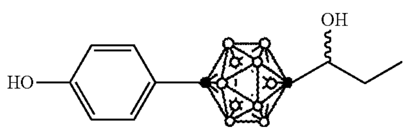 |
| 14 | 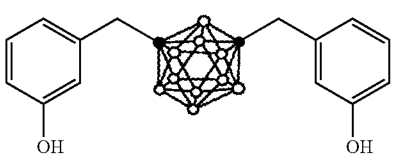 |
| 15 | 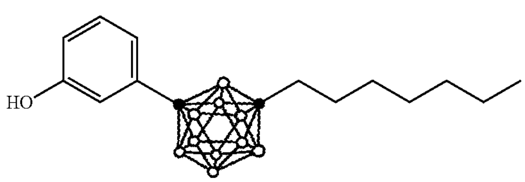 |
| 16 | 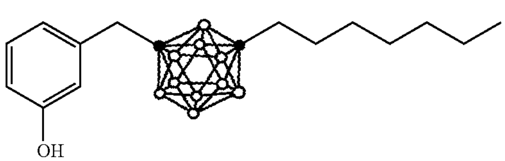 |
| 17 | 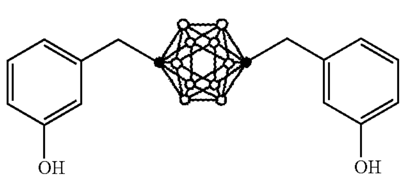 |

TABLE 2-continued

Synthesized library of compounds.

| Compound | Structure |
|---|---|
| 18 | 3-hydroxybenzyl / 3-methoxybenzyl carborane |
| 19 | 3-methoxybenzyl / 3-methoxybenzyl carborane |
| 20 | 4-hydroxyphenyl carborane with 1-hydroxy-6-methylheptyl substituent |
| 21 | 4-hydroxyphenyl carborane with heptanoyl substituent |
| 22 | 4-hydroxyphenyl carborane with (2,3-dihydro-1H-inden-5-yl)(hydroxy)methyl substituent |
| 23 | 4-hydroxyphenyl carborane with 1-hydroxy-3-phenylpropyl substituent |
| 24 | 4-hydroxyphenyl carborane with (S)-1-hydroxyheptyl substituent |
| 25 | 4-hydroxyphenyl carborane with (R)-1-hydroxyheptyl substituent |

TABLE 3

Compounds from Thirumamagal BTS et al.
Bioconj. Chem. 2006, 17, 114-1150.

| Compound | Structure |
|---|---|
| 01 | HO-phenyl-carborane-CH2CH2CH2CH2CH(CH3)2 |
| 02 | HO-phenyl-carborane-(CH2)n-CH(CH3)2 |
| 03 | HO-phenyl(meta)-carborane-(CH2)n-CH(CH3)2 |

TABLE 4

Assay description

| assay | Reporter mode | Steroid receptor | Reporter vector | Cells | Genetic modification | Cell incubation with compounds | Antagonist mode | Assay readout | Assay reagent |
|---|---|---|---|---|---|---|---|---|---|
| ERα | Agonist | Human full-length ERα | pGL4-3xERE-Luc2 | HEK293 | Transiently transfected cells | 24 hours | — | Luciferase (luminescence) | Britelite Plus (Perkin Elmer) |
| ERβ | Agonist | Human full-length ERβ | pGL4-3xERE-Luc2 | HEK293 | Transiently transfected cells | 24 hours | — | Luciferase (luminescence) | Britelite (Perkin Elmer) |
| AR | Agonist | Human full-length AR | pGL4-MMTV-Luc2 | U2OS | Stable transfectants, clone 22 | 24 hours | | Luciferase (luminescence) | Britelite (Perkin Elmer) |
| AR | Antagonist | Human full-length AR | pGL4-MMTV-Luc2 | U2OS | Stable transfectants, clone 22 | 24 hours | 2 nM Dihydro-testosterone | Luciferase (luminescence) | Britelite (Perkin Elmer) |
| GR | Agonist | Human full-length GR | pGL4-MMTV-Luc2 | U2OS | Stable transfectants, clone 26 | 24 hours | | Luciferase (luminescence) | Britelite (Perkin Elmer) |
| GR | Antagonist | Human full-length GR | pGL4-MMTV-Luc2 | U2OS | Stable transfectants, clone 26 | 24 hours | 10 nM Dexa-methasone | Luciferase (luminescence) | Britelite (Perkin Elmer) |
| Viability | — | — | — | HEK293 | — | 24 hours | | Luciferase (luminescence) | ATPlite 1 step (Perkin Elmer) |

TABLE 5

Results of in vitro testing of the compounds in ERα and ERβ cell-based reporter assays.

| compound | | ERα Log(EC$_{50}$) (M) | SD | EC$_{50}$ (nM) | Efficacy (%) | SD | ERβ Log(EC$_{50}$) (M) | SD | EC$_{50}$ (nM) | Efficacy (%) | SD | ERβ Selectivity |
|---|---|---|---|---|---|---|---|---|---|---|---|---|
| E2 | | −10.16 | 0.16 | 0.07 | 99 | 6.1 | −10.58 | 0.10 | 0.03 | 93 | 2.7 | 2.7 |
| DPN | | −5.78 | 0.11 | 1668 | 95 | 8.7 | −8.88 | 0.06 | 1.33 | 113 | 2.4 | 1252 |
| PPT | | −8.48 | 0.13 | 3.3 | 101 | 7.2 | low | | low | | | |
| 01 | | −5.11 | 0.02 | 7810 | 80 | 1.7 | low | | low | | | |
| 02 | Trial 1 | −5.49 | 0.08 | 3268 | 120 | 7.9 | −7.48 | 0.05 | 33 | 110 | 2.5 | 99 |
|  | Trial 2 | −5.17 | 0.01 | 6684 | 93 | | −6.56 | 0.07 | 277 | 95 | 4.3 | 24 |
| 03 | | −4.20 | 1.98 | 92635 | | | −5.56 | 0.07 | 2780 | 64 | 4.5 | |
| 04 | Trial 1 | −4.46 | 0.03 | 35000 | 57 | 2.7 | −5.89 | 0.01 | 1292 | 47 | 0.4 | |
|  | Trial 2 | −5.90 | 0.11 | 1251 | 113 | 9.7 | −7.10 | 0.07 | 80 | 96 | 3.4 | 16 |
| 05 | | low | | low | | | −5.22 | 0.04 | 5997 | 77 | 2.6 | |
| 06 | Trial 1 | −5.78 | 0.31 | 1647 | 30 | 9.4 | −7.71 | 0.08 | 19 | 100 | 3.5 | 85 |
|  | Trial 2 | −5.51 | 0.02 | 3092 | 66 | 1.9 | −7.76 | 0.07 | 17 | 103 | 4.0 | 177 |
| 07 | | −7.12 | 0.03 | 75 | 104 | 3.0 | −8.02 | 0.15 | 10 | 90 | 5.0 | 7.8 |
| 08 | | −4.75 | 1.09 | 17985 | | | −7.05 | 0.08 | 90 | 68 | 3.1 | 200 |
| 09 | | −4.58 | 2.61 | 26034 | | | −6.60 | 0.05 | 253 | 55 | 2.0 | 103 |

TABLE 5-continued

Results of in vitro testing of the compounds in ERα and ERβ cell-based reporter assays.

| | | ERα | | | | | ERβ | | | | |
|---|---|---|---|---|---|---|---|---|---|---|---|
| compound | | Log(EC$_{50}$) (M) | SD | EC$_{50}$ (nM) | Efficacy (%) | SD | Log(EC$_{50}$) (M) | SD | EC$_{50}$ (nM) | Efficacy (%) | SD | ERβ Selectivity |
| 10 | | low | | low | | | −6.76 | 0.07 | 175 | 55 | 3.2 | >571 |
| 11 | | −6.77 | 0.10 | 168 | 96 | 7.8 | −8.57 | 0.07 | 2.7 | 86 | 2.9 | 62 |
| 12 | Trial 1 | −7.45 | 0.08 | 36 | 101 | 4.8 | −8.89 | 0,11 | 1.3 | 85 | 4.1 | 28 |
| | Trial 2 | −7.53 | 0.09 | 30 | 94 | 5.3 | −8.94 | 0.07 | 1.14 | 104 | 2.8 | 26 |
| 13 | | −7.13 | 0.07 | 74 | 94 | 4.3 | −8.86 | 0.11 | 1.4 | 97 | 4.1 | 54 |
| 14 | | low | | low | | | low | | low | | | |
| 15 | | low | | low | | | low | | low | | | |
| 16 | | low | | low | | | low | | low | | | |
| 17 | | low | | low | | | low | | low | | | |
| 18 | | low | | low | | | low | | low | | | |
| 19 | | low | | low | | | low | | low | | | |
| 20 | | −4.89 | 0.15 | 12815 | | | −7.46 | 0.05 | 35 | 81 | 2.6 | 368 |
| 21 | | −5.55 | 0.04 | 2808 | 54 | 2.7 | −6.82 | 0.06 | 151 | 66 | 2.5 | 19 |
| 22 | | −6.07 | 0.07 | 857 | 65 | 6.0 | −7.54 | 0.08 | 29 | 32 | 1.9 | 30 |
| 23 | | −5.96 | 0.01 | 1096 | | | −7.45 | 0.03 | 36 | 75 | 1.5 | 31 |
| 24 | | −5.00 | 0.11 | 10112 | | | −7.40 | 0.04 | 40 | 91 | 1.9 | 253 |
| 25 | | −5.51 | 0.04 | 3114 | | | −7.54 | 0.06 | 29 | 8 | 2.5 | 108 |

Trial 1, Trial 2 = for compounds with multiple trials reported, Trial 2 data is believed to be more reliable, but all data reported here for completeness.
Low = activity detected, but activity was so low that exact value not reported.
>, <= exact value could not be determined from the tested concentration range.

Example 20

The family of steroid receptors consists of six highly evolutionary conserved, but structurally related receptors. Natural ligands for steroid receptors are structurally even more related and despite their high similarity, they can bind very selectively to their dedicated target. For example, cortisol is the ligand of the glucocorticoid receptor and it does not interact with estrogen receptors.

As discussed above, the library of carborane derivatives shows preferential activation of ERβ over ERα, based on profiling over a wide concentration range. It is however possible that these carborane derivatives, being a new class of artificially prepared ERβ ligands and structurally unrelated to the natural estrogen hormones, can have a different activity profile and can interact with the remaining members of the steroid receptor family, such as with androgen receptor. Such unwanted activity would have profound biological consequences.

To evaluate the off-target activities of the carborane compounds on other steroid receptors, androgen receptor (AR) and glucocorticoid receptor (GR) cell-based luciferase reporter assays were performed in the same manner as the estrogen receptor (ER) reporter assays described above (Sedlak, D. et al. *Comb. Chem. High T. Scr.* 2011, 14, 248-266). The compounds tested were E2, DPN, PPT, 01, 02, 03, 04, 05, 06, 07, 08, 09, 10, 11, 12, 13, 20, 21, 22, 23, 24, and 25. The AR and GR assay descriptions are summarized in Table 4. The assays were carried out with stable reporter cell lines expressing full-length AR or GR in the osteosarcoma U2OS cell line with no endogenous expression of these receptors. The experiment was performed in the agonist and antagonist mode to detect all possible interactions of compounds with the receptor. In the antagonist mode, dihydrotestosterone (DHT) or dexamethasone was added to the cell culture 1 hour after the compound addition to the final concentration of 2 nM or 10 nM, for the AR and GR reporter assay, respectively. In the concentration range tested (100 µM to 100 pM), no agonistic or antagonistic activities on AR or GR were detected for the tested compounds, suggesting that the activity of carborane derivatives is restricted to ERβ only.

Example 21

The in vitro cytotoxicity of the compounds was assessed by running a viability assay on HEK293 cells parallel to the ERα and ERβ reporter assays to ensure the comparability of the obtained results. The non-transfected HEK293 cells were seeded to the 384-well plates at 5000 cell/well, compounds were added and the timing of all subsequent steps was exactly the same as in the reporter assays. The compounds tested were E2, DPN, PPT, 01, 02, 03, 04, 05, 06, 07, 08, 09, 10, 11, 12, 13, 20, 21, 22, 23, 24, and 25. After 24 h of compound incubation with cells, the viability of cells was measured by determining the ATP level in the samples using luciferase cell viability assay, ATPlite 1step (Perkin Elmer, USA). The results are summarized in Table 6 and show that the compounds are non-toxic or they show a marginal cytotoxicity at the highest concentrations tested (IC$_{50}$>20 µM).

TABLE 6

Results of the in vitro cytotoxicity of the compounds in the HEK293 viability assay.

| Compound | | HEK293 viability IC$_{50}$ (µM) |
|---|---|---|
| E2 | | Low |
| DPN | | Low |
| PPT | | Low |
| 01 | | 37 |
| 02 | Trial 1 | Low |
| | Trial 2 | 42 |
| 03 | | 84 |
| 04 | Trial 1 | 25 |
| | Trial 2 | 45 |
| 05 | | Low |
| 06 | Trial 1 | 18 |
| | Trial 2 | 17 |
| 07 | | 33 |
| 08 | | 33 |

TABLE 6-continued

Results of the in vitro cytotoxicity of
the compounds in the HEK293 viability assay.

| Compound | HEK293 viability IC$_{50}$ (μM) |
|---|---|
| 09 | 35 |
| 10 | 16 |
| 11 | 34 |
| 12 Trial 1 | 34 |
| Trial 2 | 32 |
| 13 | 47 |
| 20 | 16 |
| 21 | 24 |
| 22 | 21 |
| 23 | 18 |
| 24 | 20 |
| 25 | 19 |

Trial 1, Trial 2 = for compounds with multiple trials reported, Trial 2 data is believed to be more reliable, but all data reported here for completeness.
Low = activity detected, but activity was so low that exact value not reported.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A compound defined by Formula IV, or a pharmaceutically acceptable salt thereof:

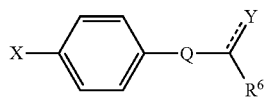

IV wherein
Q is a substituted or unsubstituted dicarba-closo-dodecaborane cluster, and

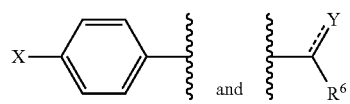

are attached to Q in a para configuration;
the dotted line to Y indicates that the bond can be a single bond or a double bond, as valence permits;
X is OH, NHR$^2$, SH, or S(O)(O)NHR$^2$;
Y is O, OR$^{2'}$, NHR$^2$, SH, or S(O)(O)NHR$^2$;
R$^6$ is substituted or unsubstituted C$_2$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, or NR$^3$R$^4$;
R$^2$ is H, OH, halogen, or substituted or unsubstituted C$_1$-C$_4$ alkyl;
R$^{2'}$ is H or substituted or unsubstituted C$_1$-C$_4$ alkyl; and
R$^3$ and R$^4$ are independently selected from substituted or unsubstituted C$_1$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, or substituted or unsubstituted C$_1$-C$_{20}$ acyl.

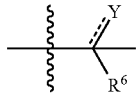

2. The compound of claim 1, wherein Q is

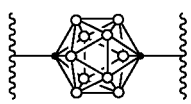

wherein
• is a carbon atom or a boron atom; and
○ is C—H, C-halogen, C-alkyl, C—OH, C—NH$_2$, B—H, B-halogen, B-alkyl, B—OH, or B—NH$_2$.

3. The compound of claim 1, wherein the compound is defined by Formula V, or a pharmaceutically acceptable salt thereof:

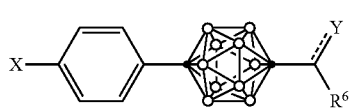

V wherein
• is a carbon atom;
○ is B—H, B-halogen, B-alkyl, B—OH, or B—NH$_2$;
the dotted line to Y indicates that the bond can be a single bond or a double bond, as valence permits;
X is OH, NHR$^2$, SH, or S(O)(O)NHR$^2$;
Y is O, OR$^{2'}$, NHR$^2$, SH, or S(O)(O)NHR$^2$;
R$^6$ is substituted or unsubstituted C$_2$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, or NR$^3$R$^4$;
R$^2$ is H, OH, halogen, or substituted or unsubstituted C$_1$-C$_4$ alkyl;
R$^{2'}$ is H or substituted or unsubstituted C$_1$-C$_4$ alkyl; and
R$^3$ and R$^4$ are independently selected from substituted or unsubstituted C$_1$-C$_{20}$ alkyl, substituted or unsubstituted C$_2$-C$_{20}$ alkenyl, substituted or unsubstituted C$_2$-C$_{20}$ alkynyl, substituted or unsubstituted C$_2$-C$_{20}$ alkylaryl, substituted or unsubstituted C$_4$-C$_{20}$ alkylcycloalkyl, or substituted or unsubstituted C$_1$-C$_{20}$ acyl.

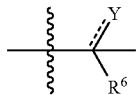

4. The compound of claim 1, wherein X is OH.
5. The compound of claim 1, wherein Y is OH.
6. The compound of claim 1, wherein Y is O.
7. The compound of claim 1, wherein R$^6$ is a substituted or unsubstituted C$_6$-C$_{10}$ alkyl.

8. The compound of claim 1, wherein $R^6$ is a substituted or unsubstituted $C_2$-$C_{15}$ alkylaryl.
9. The compound of claim 1, wherein $R^6$ is a substituted or unsubstituted $C_8$-$C_{20}$ alkylarylcycloalkyl.
10. The compound of claim 1, wherein $R^6$ is a substituted or unsubstituted branched $C_3$-$C_{10}$ alkyl.
11. A compound selected from the group consisting of:
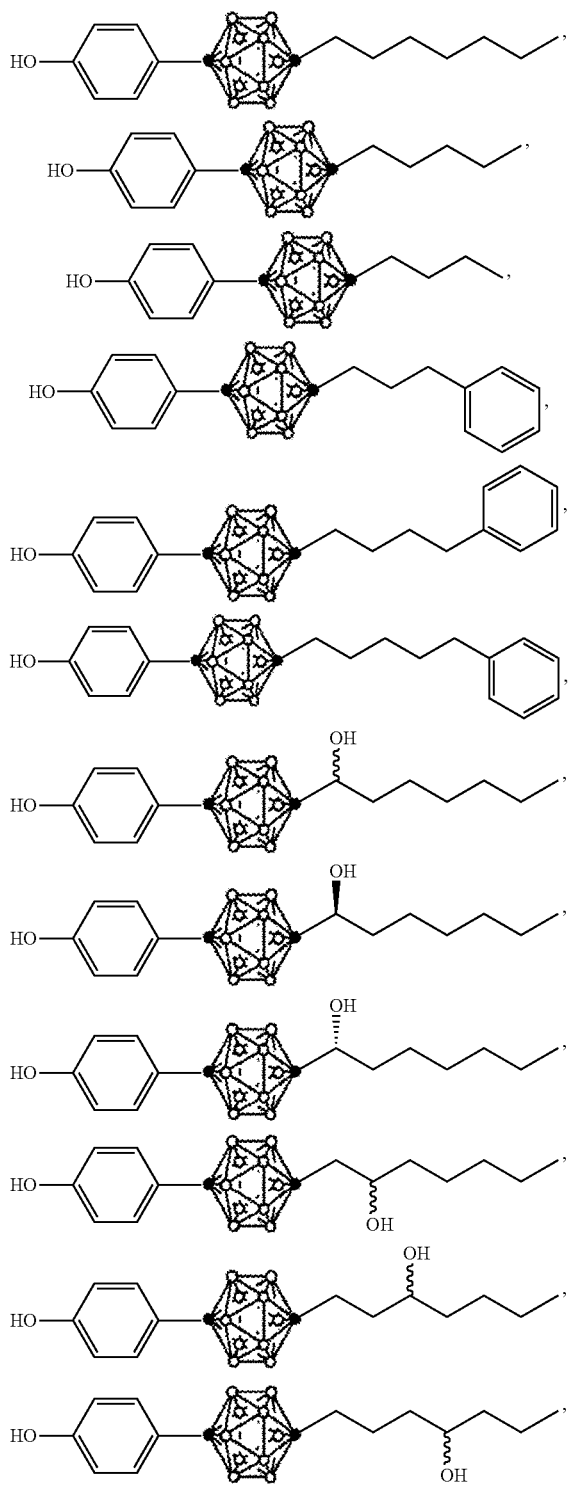
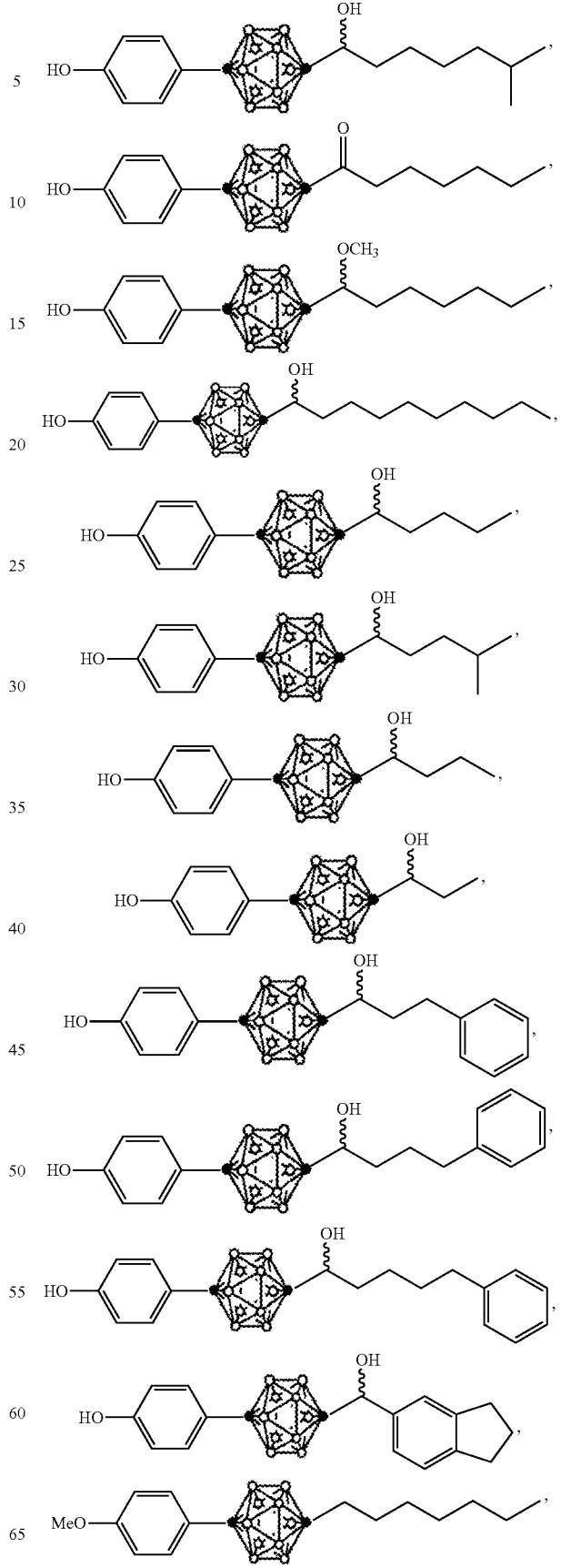

-continued

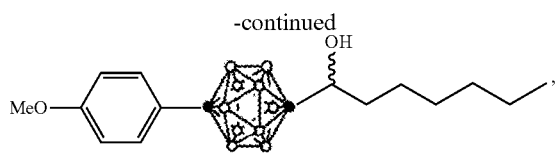

and pharmaceutically acceptable salts thereof.

12. The compound of claim 1, wherein the compound has an $EC_{50}$ of 800 nM or less at estrogen receptor beta (ERβ), an ERβ-to-ERα agonist ratio of 8 or more, or a combination thereof.

13. A pharmaceutical composition comprising a compound of claim 1 and a pharmaceutically acceptable excipient.

14. A method of treating cancer in a subject having cancer, the method comprising administering to the subject a therapeutically effective amount of a compound of claim 1.

15. A method of suppressing tumor growth in a subject, the method comprising contacting at least a portion of the tumor with a therapeutically effective amount of a compound of claim 1.

16. A method of treating an inflammatory disease in a subject having the inflammatory disease, the method comprising administering to the subject a therapeutically effective amount of a compound of claim 1.

17. A method of treating a neurodegenerative disease in a subject having the neurodegenerative disease, the method comprising administering to the subject a therapeutically effective amount of a compound of claim 1.

18. A method of treating a psychotropic disorder in a subject having the psychotropic disorder, the method comprising administering to the subject a therapeutically effective amount of a compound of claim 1.

19. A method of imaging a cell or a population of cells expressing ERβ within or about a subject, the method comprising: administering to the subject an amount of a compound of claim 1; and detecting the compound of claim 1.

20. A method comprising administering a therapeutically effective amount of a compound of claim 1 to a cell or a population of cells expressing ERβ within or about a subject.

* * * * *

UNITED STATES PATENT AND TRADEMARK OFFICE
CERTIFICATE OF CORRECTION

PATENT NO. : 11,771,712 B2
APPLICATION NO. : 17/241627
DATED : October 3, 2023
INVENTOR(S) : Werner Tjarks, Petr Bartunek and David Sedlak Page 1 of 1

It is certified that error appears in the above-identified patent and that said Letters Patent is hereby corrected as shown below:

In the Claims

Claim 1, Column 68, Line 6-10 (approx.), below "acyl." delete " 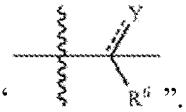 ".

Claim 3, Column 68, Line 54, delete "C4.C20" and insert -- C4-C20 --.

Claim 3, Column 68, Line 56-60 (approx.), below "acyl." delete " 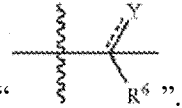 ".

Signed and Sealed this
Twenty-seventh Day of August, 2024

Katherine Kelly Vidal
*Director of the United States Patent and Trademark Office*